US011535871B2

(12) United States Patent
Junge et al.

(10) Patent No.: US 11,535,871 B2
(45) Date of Patent: Dec. 27, 2022

(54) OPTIMIZED GENE EDITING UTILIZING A RECOMBINANT ENDONUCLEASE SYSTEM

(71) Applicant: University of Southern California, Los Angeles, CA (US)

(72) Inventors: Jason Junge, South Pasadena, CA (US); Timothy Hunt, Seattle, WA (US); Scott E. Fraser, Glendale, CA (US)

(73) Assignee: University of Southern California, Los Angeles, CA (US)

( * ) Notice: Subject to any disclaimer, the term of this patent is extended or adjusted under 35 U.S.C. 154(b) by 232 days.

(21) Appl. No.: 15/573,732

(22) PCT Filed: May 13, 2016

(86) PCT No.: PCT/US2016/032367
§ 371 (c)(1),
(2) Date: Nov. 13, 2017

(87) PCT Pub. No.: WO2016/183448
PCT Pub. Date: Nov. 17, 2016

(65) Prior Publication Data
US 2018/0127785 A1    May 10, 2018

Related U.S. Application Data

(60) Provisional application No. 62/161,487, filed on May 14, 2015.

(51) Int. Cl.
| C12N 15/90 | (2006.01) |
| C12N 9/22 | (2006.01) |
| C12N 15/85 | (2006.01) |
| C07K 14/435 | (2006.01) |
| C12N 15/11 | (2006.01) |
| C12N 15/10 | (2006.01) |

(52) U.S. Cl.
CPC ...... *C12N 15/907* (2013.01); *C07K 14/43504* (2013.01); *C12N 9/22* (2013.01); *C12N 15/102* (2013.01); *C12N 15/11* (2013.01); *C12N 15/85* (2013.01); *C07K 2319/60* (2013.01); *C07K 2319/80* (2013.01); *C07K 2319/81* (2013.01); *C12N 2310/20* (2017.05); *C12N 2800/80* (2013.01)

(58) Field of Classification Search
CPC .... C12N 9/22; C12N 2310/20; C12N 15/907; C12N 15/102; C07K 2319/80; C07K 2319/81
See application file for complete search history.

(56) References Cited

U.S. PATENT DOCUMENTS

| 7,951,925 B2 * | 5/2011 | Ando | A61P 37/00 536/23.1 |
| 8,313,925 B2 * | 11/2012 | Gregory | A61K 48/0008 435/358 |
| 9,023,649 B2 | 5/2015 | Mali et al. | |
| 9,394,531 B2 * | 7/2016 | Miller | C12N 9/22 |
| 9,746,475 B2 | 8/2017 | Arnold et al. | |
| 10,190,106 B2 * | 1/2019 | Wolfe | C12N 9/22 |
| 2002/0160940 A1 * | 10/2002 | Case | A61P 31/18 514/1.2 |
| 2008/0159996 A1 * | 7/2008 | Ando | A61P 37/00 435/375 |
| 2013/0326645 A1 * | 12/2013 | Cost | C12N 15/8213 800/14 |
| 2014/0068797 A1 * | 3/2014 | Doudna | C12N 15/70 435/375 |
| 2014/0287426 A1 | 9/2014 | Arnold et al. | |
| 2014/0356958 A1 | 12/2014 | Mali et al. | |
| 2015/0044772 A1 | 2/2015 | Zhao | |
| 2015/0064789 A1 | 3/2015 | Paschon et al. | |
| 2015/0067922 A1 | 3/2015 | Yang et al. | |

(Continued)

FOREIGN PATENT DOCUMENTS

| CN | 107614680 A | 1/2018 |
| EP | 2392208 A1 | 12/2011 |

(Continued)

OTHER PUBLICATIONS

Holt et al. Human hematopoietic stem/progenitor cells modified by zinc-finger nucleaes targeted to cCR5 control HIV-1 in vivo. Nature Biotechnology, vol. 28, No. 8, pp. 839-847, Aug. 2010, including pp. 1/2-2/2 of Online Methods. (Year: 2010).*

Jinek et al. RNA-programmed genome editing in human cells. eLife, vol. 2, e00471, Jan. 29, 2013, printed as pp. 1/9-9/9. (Year: 2013).*

Anders et al. Structural basis of PAM-dependent target DNA recognition by the Cas9 endonuclease. Nature, vol. 513, pp. 569-579, Sep. 2014, including pp. 1/2-2/2 of Online Methods, and pp. 1/9-9/9 of Extended Data. (Year: 2014).*

Zetsche et al. Cpf1 is a single RNA-guided endonuclease of a class 2 CRISPR-Cas system. Cell, vol. 163, pp. 759-771, Oct. 22, 2015. (Year: 2015).*

(Continued)

*Primary Examiner* — Jennifer Dunston
(74) *Attorney, Agent, or Firm* — Nixon Peabody LLP; Linda B. Huber

(57) ABSTRACT

Described herein are methods and compositions for genomic editing. Endonucleases for genomic editing involve inducing breaks in double stranded DNA, for which knock-ins are notoriously inefficient for relying on random integration of homologous DNA sequences into the break site by repair proteins. To address these issues, described herein are novel recombinant fusion proteins that actively recruit linear DNA inserts in closer proximity to the genomic cleavage site, increasing integration efficiency of large DNA fragments into the genome. Such improvements to genomic editing technology allow one to use lower linear DNA concentrations without sacrificing efficiency and can be further combined with other features, such as fluorescent protein reporting systems.

11 Claims, 8 Drawing Sheets

Specification includes a Sequence Listing.

(56) References Cited

U.S. PATENT DOCUMENTS

| | | | |
|---|---|---|---|
| 2016/0208243 A1* | 7/2016 | Zhang | C12N 15/10 |
| 2018/0250424 A1* | 9/2018 | Cotta-Ramusino | C12N 15/113 |

FOREIGN PATENT DOCUMENTS

| | | | |
|---|---|---|---|
| EP | 3294879 | 3/2018 | |
| WO | 2009154686 A1 | 12/2009 | |
| WO | WO-2014099744 A1 * | 6/2014 | C12N 15/8201 |
| WO | WO-2016054326 A1 * | 4/2016 | C12N 15/102 |
| WO | 2016/183448 A1 | 11/2016 | |

OTHER PUBLICATIONS

Mussolino et al. RNA guides genome engineering. Nature Biotechnology, vol. 31, No. 3, p. 208, Mar. 2013. (Year: 2013).*

Mali et al. RNA-guided human genome engineering via Cas9. Science, vol. 339, pp. 823-826, Feb. 2013. (Year: 2013).*

Makarova et al. Evolution and classification of the CRISPR-Cas systems. Nature Reviews. Microbiology, vol. 9, No. 6, pp. 467-677, 2011, printed as pp. 1-23. (Year: 2011).*

Ran, F.A. Adaptation of CRISPR nucleases for eukaryotic applications. Analytical Biochemistry, vol. 532, pp. 90-94, 2017, available online Oct. 27, 2016. (Year: 2016).*

Hockenmeyer et al. Efficient targeting of expressed and silent genes in human ESCs and iPSCs using zinc-finger nucleases. Nature Biotechnology, vol. 27, No. 9, pp. 851-857, Sep. 2009, including pp. 1/2-2/2 of Online Methods. (Year: 2009).*

Klug et al. The discovery of zinc fingers and their applications in gene regulation and genome manipulation. Annual Review of Biochemistry, vol. 79, pp. 213-231, 2010. (Year: 2010).*

Kang et al. CCR5 disruption in induced pluripotent stem cells using CRISPR/Cas9 provides selective resistance of immune cells to CCR5-tropic HIV-1 virus. Molecular Therapy. Nucleic Acids, vol. 4, e268, Dec. 15, 2015, printed as pp. 1-10. (Year: 2015).*

Yao et al. Human Gene Therapy, vol. 23, pp. 238-242, Feb. 2012, including pp. 1/2-2/2 of Supplementary Data. (Year: 2012).*

International Search Report and Written Opinion for PCT/US2016/032367 dated Sep. 2, 2016, 8 pages.

Nissim et al., Multiplexed and Programmable Regulation of Gene Networks with an Integrated RNA and CRISPR/Cas Toolkit in Human Cells, Mol. Cell., 2014, vol. 54(4), pp. 698-710.

International Preliminary Report on Patentability for PCT/US2016/032367 dated Nov. 14, 2017, 6 pages.

Supp European Search Report for EP 16793610 dated Jan. 15, 2019 (8 pages).

Fonfara et al., Creating highly specific nucleases by fusion of active restriction endonucleases and catalytically inactive homing endonucleases, Nucleic Acids Research, 2001, 14 pages.

EP 16793610.3 Examination Report dated Feb. 7, 2020, 5 pages.

Hruscha, A. et al., Efficient CRISPR/Cas9 genome editing with low off-target effects in zebrafish, The Company of Biologists Ltd/Development, 2013, 140:4982-4987.

Zu, Y. et al., TALEN-mediated precise genome modification by homologous recombination in zebrafish, Nature America, Inc., 2013, DOI:10.1038, 4 pages.

\* cited by examiner

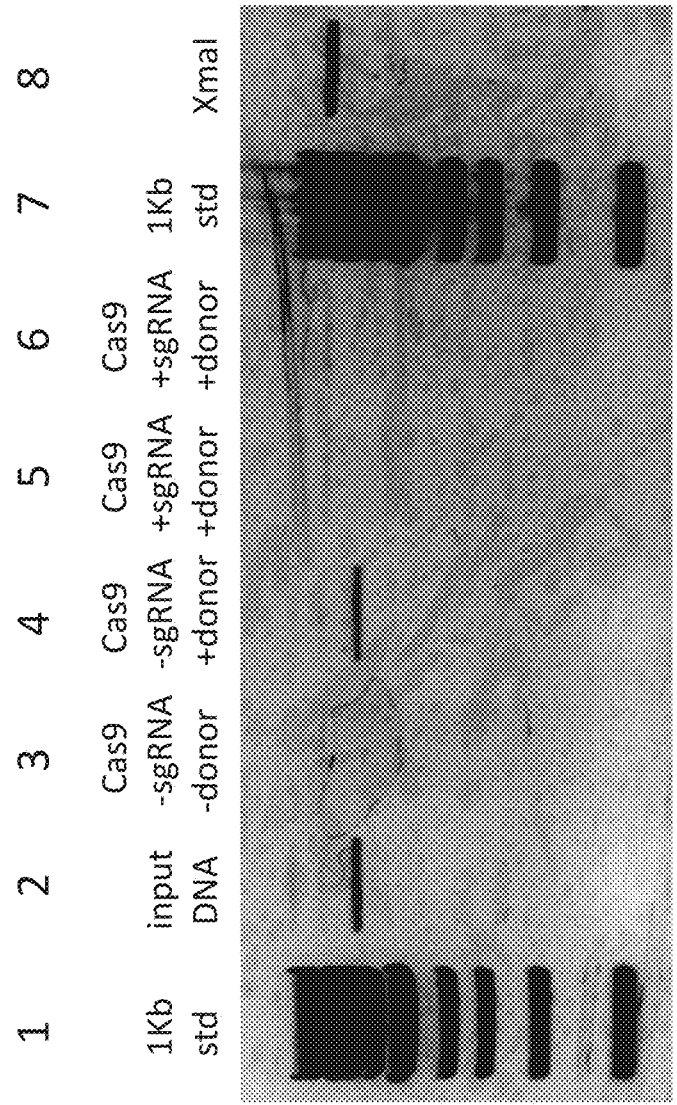

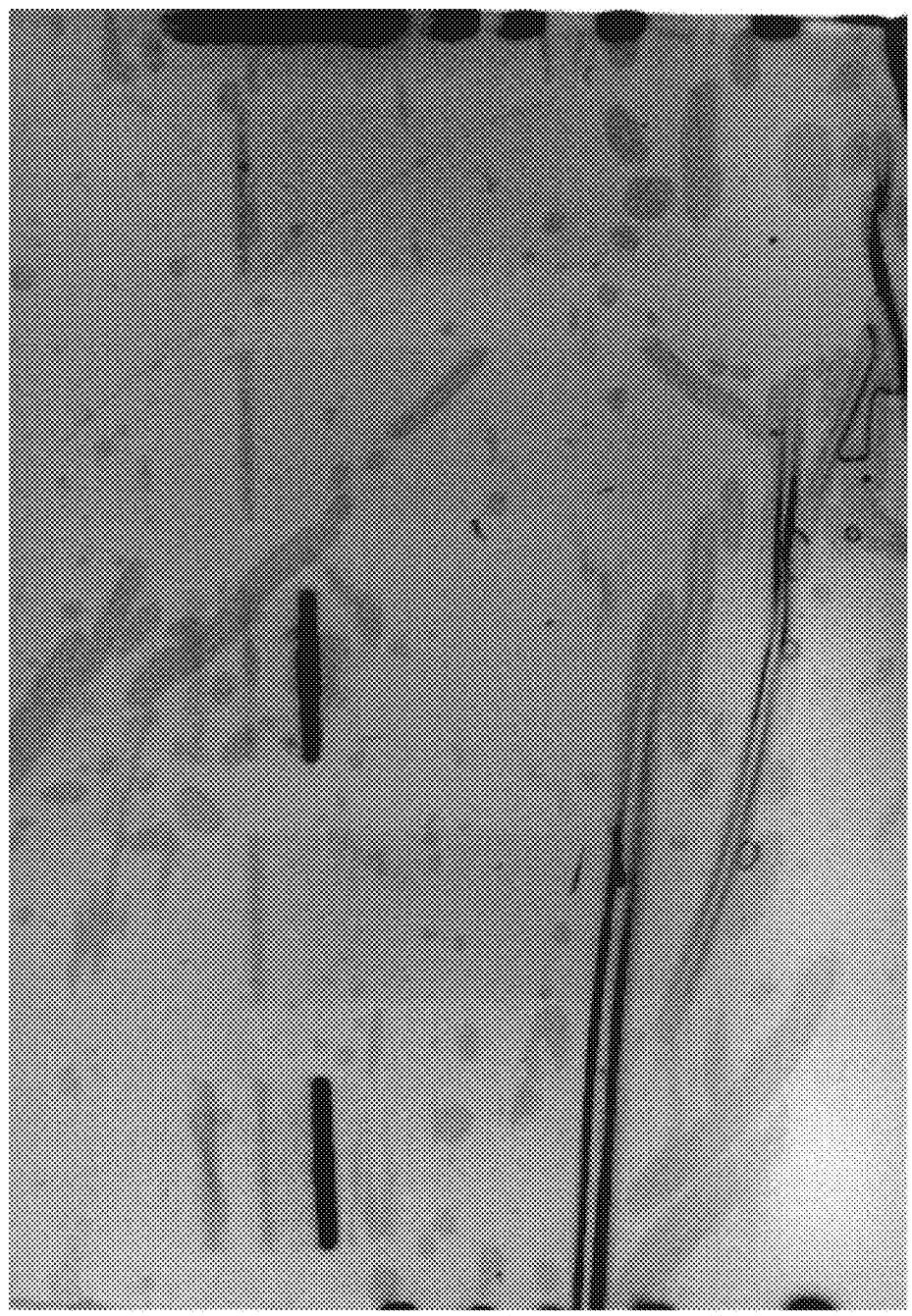

OPTIMIZED GENE EDITING UTILIZING A RECOMBINANT ENDONUCLEASE SYSTEM

CROSS-REFERENCE TO RELATED APPLICATIONS

This application is a National Phase of International Application No. PCT/US2016/032367 filed May 13, 2016, which designated the U.S. and that International Application was published under PCT Article 21(2) in English, which also includes a claim of priority under 35 U.S.C. § 119(e) to U.S. provisional patent application No. 62/161,487 filed May 14, 2015, the entirety of which is hereby incorporated by reference.

REFERENCE TO SEQUENCE LISTING

The Sequence Listing submitted Oct. 2, 2020, as a text file named "AmendedSequenceListing-065715-000063US00_ST25.txt" created on Sep. 1, 2020 and having a size of 25,114 bytes, is hereby incorporated by reference, which includes no new matter and replaces the sequence listing submitted in a PDF file and a text file on Nov. 13, 2017.

FIELD OF THE INVENTION

Described herein are methods and compositions for use in in vitro and in vivo manipulation of genetic sequences for research and therapeutic activities, including generation of knockout and knock-in sequences for genomic editing.

BACKGROUND

CRISPR-Cas genome editing has become a more mature technique within the last 10 years. Like all other genome editing techniques, it is adequate at generating knockout phenotypes, but not very efficient at introducing knock-in of donor DNA sequences. The development of more useful enzymes for biotechnology and primary research has included improving efficacy of enzymes, creating new enzymes to fill needs, or adapting them to expand their functionality. For example, Klenow exonuclease minus enzyme is a truncation of the Klenow large-fragment. This modified DNA polymerase retains its polymerase activity while losing the large-fragment's ability to chew back 3' DNA overhangs. Another example includes PHUSION® DNA polymerase, a proprietary fusion protein consisting of a proofreading DNA polymerase plus the domain of another DNA polymerase that confers higher copying rate. Extending these principles to the realm of genome editing, it should be possible to create a new Cas-9 protein that preserves the existing DNA endonuclease activity while increasing the integration efficiency of donor DNA sequence into the genome. Several strategies are proposed to address this need.

There are several obstacles in particular that concern insertion of donor DNA into the genome. Non-homologous end joining (NHEJ), while an appropriate method for knocking out genes, is wholly insufficient for integration of donor DNA without the presence of any other mutations. Homology directed repair (HDR) encompasses at least two forms: a long sequence homology arm requiring Holliday structures to resolve integrations, or short homology arms which rely on strand invasion and the emergency DNA repair system to resolve the integration events. Any combination of HDR and NHEJ will predominantly yield indel (insertion and deletion) mutations within the portion of the damaged DNA resolved by NHEJ. In essence, stochastic processes determine the possible integration of homologous DNA and plague efficient genomic editing for knock-ins, including the inversely proportional relationship between the length of the donor DNA fragment and the efficiency of integration, integration efficiency of donor DNA is directly proportional to the donor DNA concentration in the cell and cytotoxic overabundance of linear DNA fragments, and spatial restriction of the two free ends of a double stranded break therefore causing a most likely outcome of re-annealing of the two ends.

Described herein is the development of recombinant fusion protein that actively recruit linear DNA inserts in closer proximity to the genomic cleavage site, thereby allowing increasing integration efficiency, particularly of large DNA fragments, into the genome. Such improvements to genomic editing technology allow one to use lower linear DNA concentrations without sacrificing efficiency and can be further combined with other features, such as fluorescent protein reporting systems.

SUMMARY OF THE INVENTION

Described herein is a composition including a vector encoding a fusion protein including at least one endonuclease and a DNA binding moiety. In various embodiments, the fusion protein includes at least one endonuclease selected from the group consisting of: cas regularly interspaced short palindromic (CRISPR) protein, a zinc finger nuclease (ZFNs) and transcription activator-like effector nucleases (TALENs). In various embodiments, the CRISPR protein includes cas9. In various embodiments, the DNA binding moiety includes a zinc finger protein. In various embodiments, the zinc finger includes a left handed CCR5 binding protein. In various embodiments, the at least one endonuclease and DNA binding moiety are joined by a linker including two, three, four, five, six, seven, eight, nine, ten or more amino acids. In various embodiments, the fusion protein includes a fluorescent labeled protein. In various embodiments, the fluorescent labeled protein includes one or more proteins selected from the group consisting of: green fluorescent protein (GFP), enhanced (eGFP), red fluorescent protein (RFP) and mCherry. In various embodiments, the fusion protein includes a nuclear localization signal (NLS). In various embodiments, the NLS is SV40 NLS.

Further described herein is a method of genomic editing including (a) providing a quantity of one or more vectors encoding a fusion protein including at least one endonuclease and a DNA binding moiety and (b) contacting a population of cells with the quantity of the one or more vectors, wherein the fusion protein is capable of inducing double stranded break (DSB) and homologous recombination (HR) of the DSB results in editing of the genome of the population of cells. In various embodiments, the method includes contacting the population of cells with one or more guide RNAs (gRNAs) in step (b). In various embodiments, the method includes contacting the population of cells with template DNA in step (b). In various embodiments, the template DNA includes at least one expression cassette, two flanking sequences, and a DNA binding moiety sequence. In various embodiments, the two flanking sequences are each at least 10 bp, and homologous to sequences in the genome of the population of cells. In various embodiments, the DNA binding moiety sequence includes CCR5. In various embodiments, contacting the population of cells includes a technique selected from the group consisting of: transfection, electroporation, and transformation. In various embodiments, the population of cells includes stem cells or progenitor cells.

Described herein is a kit for genomic editing including one or more vectors encoding a fusion protein including at least one endonuclease and a DNA binding moiety and template DNA including at least one expression cassette, two flanking sequences, and a DNA binding moiety sequence. In various embodiments, the kit includes one or more guide RNAs (gRNAs). In various embodiments, the kit fusion protein includes at least one endonuclease CRISPR protein, a DNA binding moiety that is a zinc finger protein. In various embodiments, the kit includes a fluorescent labeled protein. In various embodiments, the kit includes a nuclear localization signal (NLS).

Also described herein is a method of multi-locus genomic editing including inducing sticky end formation at one or more loci by adding a CRISPR protein, providing a quantity of one or more guide strand RNAs, ligating one or more single-stranded donor DNA, hybridizing one or more double-stranded DNA with a terminating oligonucleotide, synthesis of one or more double stranded DNA from the one or more single-stranded donor DNA to the one or more double-stranded DNA completing the donor DNA strand to form a sticky end, and joining compatible sticky ends at one or more loci.

BRIEF DESCRIPTION OF THE FIGURES

FIGS. 5A and 5B: Cas9-zinc finger fusion protein linearizes plasmid DNA efficiently. It appears there off-target cleavage that occurs perhaps due to the zinc finger, although off-target cleavage is ameliorated when the donor DNA is included. Lanes 5 and 6 are one sample loaded into two wells because well 5 was partially occluded.

DETAILED DESCRIPTION OF THE INVENTION

Figure 1:
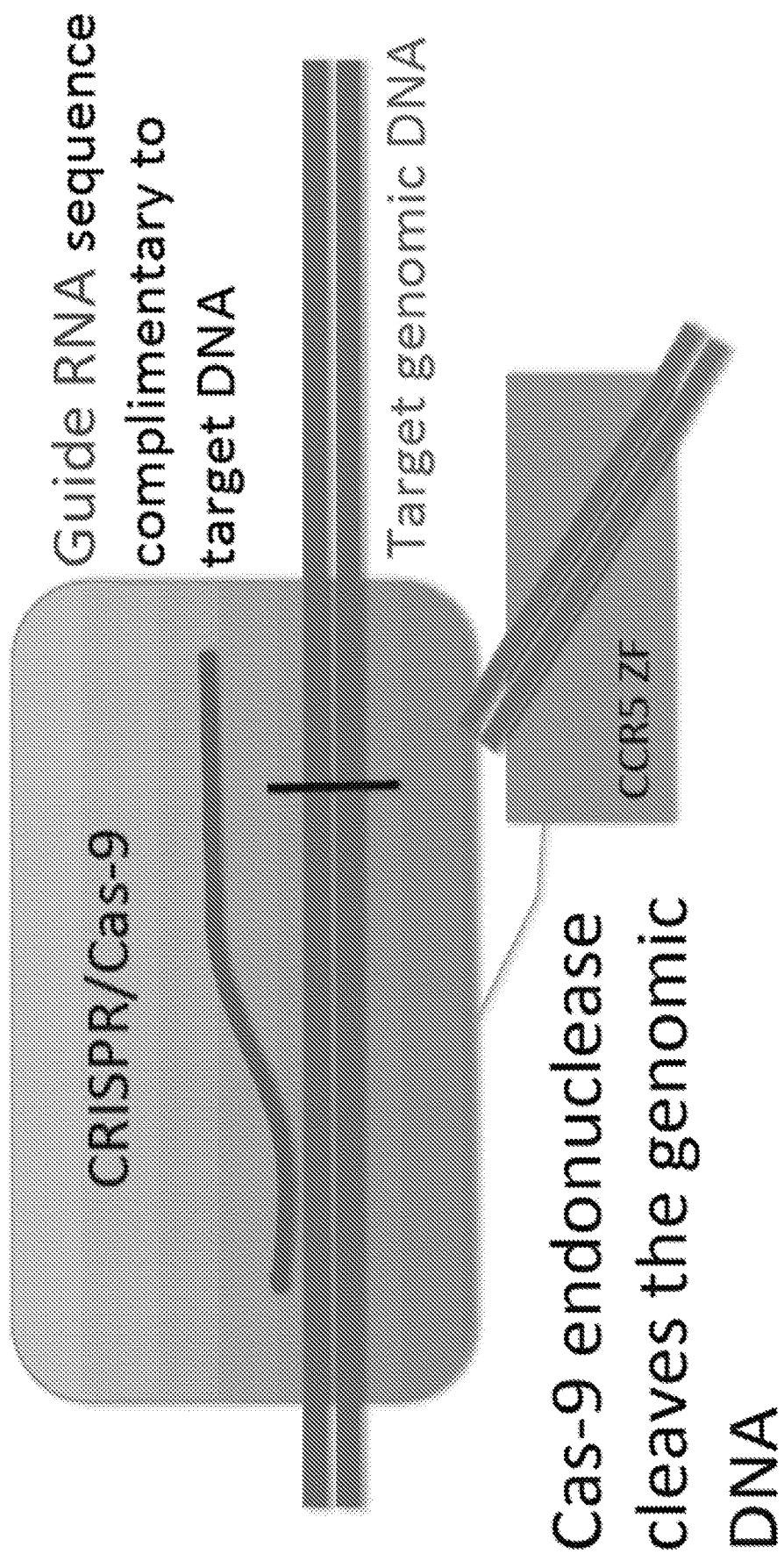
FIG. 1. Recombinant Cas-9 design. Conventionally, guide RNA (gRNA) is complementary to target DNA, and Cas-9 endonuclease cleaves the genomic, with stochastic processes determining the possible integration of homologous DNA. To shunt these processes towards favorable recombination events, a recombinant fusion protein including CCR5 zinc-finger as a DNA binding moiety to bind the homologous linear DNA fragment to be inserted, and bringing the fragment closer to the double stranded break (DSB). A recombinant Cas-9 that aids in increasing proximity of DSB and linear DNA will lead to more efficient generation of genome editing.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3rd ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods described herein. For purposes of the present invention, the following terms are defined below.

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

"Modulation" or "modulates" or "modulating" as used herein refers to upregulation (i.e., activation or stimulation), down regulation (i.e., inhibition or suppression) of a response or the two in combination or apart.

"Pharmaceutically acceptable carriers" as used herein refer to conventional pharmaceutically acceptable carriers useful in this invention.

"Promote" and/or "promoting" as used herein refer to an augmentation in a particular behavior of a cell or organism.

"Subject" as used herein includes all animals, including mammals and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

Genome editing has been a hot area of research for the past decade with an emphasis on generating genetic knockouts for genes of interest within model animals. Most methods for knocking in donated genetic sequences have typically relied on either brute force methods with random sites of integration or on homologous recombination events. Some of these techniques only work in defined model organisms, while others have only limited application. Therefore, a more wide-ranging and efficient toolbox for the integration of donor DNA with sequences ranging from 300-3,500 bp in length would present solutions for answering certain questions within biology, more rapid generation of useful transgenic animals, and making theranostics cheaper, faster, and more accessible to clinicians and their patients. This toolbox could make even a small lab more efficient at making "footprint-free" transgenic cell lines/animals using industry standard cell culture techniques, quickly, and with fewer attempts at a reasonable overhead cost.

A fundamental concern regarding donor DNA integration, on top of the problems addressed previously about mutations peri-integration, is the inversely proportional relationship between the length of the donor DNA fragment and the efficiency of integration. It has been reported that 27 and 54 bases of inserted donor DNA sequence with 41 and 49 bases of sequence homology flanking those 27 bases (117 total length) or 33 base pairs on either side of 54 base pairs (120 bp total) result in the following efficiencies: 64% mutation rate, 3.2% integration rate, with half of those lacking other mutations for the 117 base donor DNA; and 86% mutation rate, 15.6% integration, with 3.5% precise integration. Other have used TALEN endonucleases combined with very creative mathematics to report a mutation rate of 0% and a 50% integration rate (but using worst case scenario could be as low as 8.9%) and 1.5% germline transmission of 700 bases encoding GFP flanked by 827 bases and 904 bases of homology to the integration site.

Second, integration efficiency of donor DNA into the genome is directly proportional to the donor DNA concentration in the cell. The more abundant a fragment is in the cell, the more likely it is to participate in the DNA repair mechanism. A problem arises from overabundance of linear DNA fragments causing cytotoxicity due in large part to the innate ability of cells to defend themselves against DNA viruses, and also to saturating the cell's ability to recover from the endonuclease damage. The inability of a cell to discriminate between damaged DNA ends and the donor DNA ends could leave the genomic DNA unrepaired.

Third, the nucleus of a cell is a structure densely packed with genomic DNA. The two free ends of a double stranded break in the genomic DNA are spatially restricted, cannot diffuse away from each other, and therefore the most likely outcome is re-annealing of the two ends with some sequence added and/or removed at the locus of endonuclease activity. Genomic Editing. What has been shown up to this point is that genome engineering is versatile and powerful tool to correct genetic mutations. Site-specific chromosomal integration can target desired nucleotide changes, including introducing therapeutic gene cassettes in safe landing sites within chromosomes, disrupting the coding or non-coding regions of specific alleles and correcting the genetic mutations to reverse the disease phenotype. Conventional technologies such as Zinc Finger Nuclease (ZFNs) and Transcription Activator-Like Effector Nucleases (TALENs) have provided a significant groundwork of proof-of-concept studies for genome editing and therapy. Yet, the most recent advances in Clustered Regularly Interspaced Short Palindromic Repeats (CRISPR) and CRISPR-associated endonuclease protein (cas) system extend this versatility and convenience by reducing the number of steps required for designing targeting of a particular mutation.

Briefly, genome editing using tools such as ZFNs can be based on the introduction of a site-specific DNA double stranded break (DSB) into the locus of interest. Key to this process is the cellular repair mechanism for efficiently repairing DSBs via the homology-directed repair (HDR), or non-homologous end joining (NHEJ) pathways. The mechanisms of these DNA repair pathways can generate defined genetic outcomes. More specifically, genome editing using ZFNs can be based on the introduction of a site-specific DNA DSB into the locus of interest. Thereafter, NHEJ repair, can rapidly and efficiently ligate two broken ends, providing opportunity for the gain or loss of genetic information. This feature can be exploited to introduce small insertions and/or deletions at the site of the break, thereby allowing disruption of a target gene. If, for example, a disease results from toxic protein buildup, instruction of a nonsense or missense sequence effectively eliminates aberrant protein to correct human disorders caused by inherited gene defects. Alternatively, if a specifically-designed homologous donor DNA is provided in combination with the ZFNs, this template can result in gene correction or insertion, as repair of the DSB can include a few nucleotides changed at the endogenous site or the addition of a new gene at the break site.

While pioneering much of what is known about genomic editing process, significant challenges exist with conventional technologies such as ZFNs, and TALENs. These early generation nucleases, ZFNs and TALENs are artificial fusion proteins composed of an engineered DNA binding domain fused to a non-specific nuclease cleavage domain from the FokI restriction enzyme. Zinc finger and transcription activator-like effector repeat domains with customized specificities can be joined to bind to extended DNA sequences. While adaptation of ZFNs and TALENs by modifying the DNA-binding specificities provide a significant level of targeting control, individual zinc finger domains provide some heterogeneity requiring some context-dependence for DNA binding. TALE repeat domains appear less susceptible to these context-dependent effects and can be modularly assembled to recognize virtually any DNA sequence via a simple one-to-one code between individual repeats and the four possible DNA nucleotides, but assembly of DNAs encoding large numbers of highly conserved TALE repeats can require the use of non-standard molecular biology cloning methods.

Whereas both ZFNs and TALENs involving use protein—DNA interactions for targeting, bacterial CRISPR-Cas system is unique and flexible due to utilization of RNA as the moiety that targets the nuclease to a desired DNA sequence. In contrast to ZFN and TALEN platforms, CRISPR-CAS uses simple Watson-Crick base pairing rules between an engineered RNA and the target DNA site. Generally, two components form the core of a CRISPR nuclease system, a Cas nuclease (e.g., cas9) and a guide RNA (gRNA), the gRNA derived from a fusion of CRISPR-derived RNAs ("crRNA") and trans-acting antisense RNA ("tracRNA"). In the most well-studied example, the single gRNA complexes with a cas protein (e.g., cas9) to mediate cleavage of target DNA sites that are complementary to the first (5') 20 nts of the gRNA and that lie next to a protospacer adjacent motif ("PAM") sequence (canonical form of 5'-NGG for *Streptococcus pyogenes* cas9, but also alternate 5'-NAG exist). Thus, with this system, Cas9 nuclease activity can be directed to any DNA sequence of the form N20-NGG simply by altering the first 20 nts of the gRNA to correspond to the target DNA sequence. It is notes that Type II CRISPR systems from other species of bacteria recognize alternative PAM sequences and that utilize different crRNA and tracrRNA sequences could also be used to perform targeted genome editing.

The Cas9-induced DSBs have been used to introduce NHEJ-mediated indel mutations as well as to stimulate HDR with both double-stranded plasmid DNA and single-stranded oligonucleotide donor templates. The capability to introduce DSBs at multiple sites in parallel using the Cas9 system is a unique advantage of this platform relative to ZFNs, or TALENs. For example, expression of Cas9 and multiple gRNAs has been used to induce small and large deletions or inversions between the DSBs, to simultaneously introduce parallel genetic editing mutations altering different genes in rats, mouse ES cell clones, and zebrafish. Together, these advances in CRISPR/cas-mediated gene editing technology can accelerated the pace of gene-function relationship discovery, and a focused approach for developing personalized therapeutics.

An alternative is the use of Cpf1 a putative class 2 CRISPR effector with features distinct from Cas9. Cpf1 is a single RNA-guided endonuclease that does not require use of tracrRNA. Instead, it utilizes a T-rich protospacer-adjacent motif, TTTN (SEQ ID NO:11), and on the 5' side of the guide. As a result, the cut CPF1 makes is staggered, occurring 19 bp after the PAM on the targeted+strand, and 23 bp on the opposite strand. Cpf1 generates a staggered cut with a 5' overhang, in contrast to the blunt ends generated by Cas9. This allows for editing through non-homologous end joining (NHEJ). Being able to program the exact sequence of a sticky end would allow researchers to design the DNA insert so that it integrates in the proper orientation. As_Cpf1 (from Acidaminococcus) and LbCpf1 (from Lachnospiraceae) have been demonstrated as possessing genomic editing capacity in human cells.

The elegance of the CRISPR/Cas or CRISPR/Cpf1 system is allowing for tailoring to target the patient's particular mutation, combined with a delivery system via adeno-associated virus ("AAV"), or also via adenovirus, vectors as optimal vehicles for genome editing machinery can deliver components directly to the organ or cells of interest. There have been limited reports that, for example, systemic injection of an AAV vector carrying a zinc-finger nuclease and donor template construct was able to correct mutant transgenic clotting Factor IX in mice and reconstitute low but clinically detectable levels of circulating protein. In this regard, an AAV-CRISPR system could be delivered to treat dominant mutations via the same gene correction mechanism used for recessive mutations, compactly deliver targeted genomic editing machinery with a limited footprint capable of being delivered via viral vectors, as constant and agnostic to the size of the target gene and maintain the endogenous gene expression stoichiometry. These and other advantages of CRISPR/Cas, CRISPR/Cpf1 editing give it a wide range of possible clinical applications.

Thus, for any genome editing system with engineered nucleases, the use of an endonuclease joined to a DNA binding moiety such as zinc finger protein that binds donor DNA, or other methods to associate a donor DNA. The proximity of donor DNA and the double stand break leads to increased integration efficiency of the donor DNA.

Despite these advances, a paramount technical problem remains the low integration efficiency of donor DNA using genome editing tools. Herein, the Inventors describe a solution based on the realization that it is possible to bring the donor DNA in close proximity to the site of the double stranded break in the genomic DNA. This can be accomplished through creation of a Cas9:DNA-binding protein motif fusion. By recruiting the donor DNA to the cleavage site, it is possible to use a donor DNA concentration that is non-toxic to cells and yet providing a local donor DNA concentration that should improve integration efficiency. Because the donor DNA is held in such close proximity to the damaged DNA, one can engineer the sequence homology arms on both ends of the donor DNA to be relatively short (<100 bp) such that the cell's SOS DNA repair system favors the: 5'-3' exonuclease V trimming, RPA coating of the single strand DNA, 3' strand invasion, 3' end trimming by exonucleases Rad1/Rad10, and DNA nick ligation to repair the DNA versus pure Holliday junction dependent homologous recombination. Exploiting this type of DNA repair, if a favored result, will have a robust genome editing system which can be further optimized for integration of very large donor DNA fragments. By shunting stochastic processes towards favorable recombination events, recombinant fusion proteins aid in increasing proximity of DSB and linear DNA for more efficient genome editing.

In order for this increased integration efficiency to take place, the donor DNA must be in a position that is as close, or closer, to the site of DNA damage than the two opposing ends of the damaged genomic DNA are to each other. Recruitment of the donor DNA to these sites is performed either by direct or indirect association of the donor DNA with the enzymatically active Cas-9 RNA-dependent endonuclease. These DNA binding elements entail specific domains or full-length proteins in their entirety, including but not limited to these naturally occurring or engineered examples: transcription factors, endonucleases, zinc fingers, TALENs, endonuclease-minus Cas-9+guide strand RNA, or other such ribonucleoprotein that can bind directly or indirectly to specific DNA sequences. Some, but certainly not all, of the possible configurations of Cas9-endonuclease and donor DNA binding elements are: direct fusion, association (multimerization domains like leucine zippers, fkbp/FRB, etc.), engineered association via antibody mimetics, or any synthetic macromolecule (carbohydrate-, protein-, or lipid-based) which bind to Cas9 endonuclease and also bind to the donor DNA in a sequence specific manner. Preliminary results suggest this modified Cas-9 works much better than wild-type Cas-9 in generating knock-in gene modifications in cell lines.

Described herein is a composition including a vector encoding a fusion protein including at least one endonuclease and a DNA binding moiety. In various embodiments, the fusion protein endonuclease includes at least one endonuclease selected from the group consisting of: cas regularly interspaced short palindromic (CRISPR) protein, a zinc finger nuclease (ZFNs) or transcription activator-like effector nucleases (TALENs). In other embodiments, the DNA binding moiety includes a zinc finger protein. In other embodiments, the fusion protein includes at least one endonuclease CRISPR protein and a DNA binding moiety zinc finger protein. In other embodiments, the zinc finger protein includes a left handed, right handed, or both zinc fingers. In other embodiments, the zinc finger includes a left handed CCR5 sequence. In other embodiments, DNA binding moieties can include specific domains or full-length proteins in their entirety, including transcription factors, endonucleases, zinc fingers, TALENs, endonuclease-minus Cas-9+guide strand RNA, or other such ribonucleoprotein that can bind directly or indirectly to specific DNA sequences. In other embodiments, the at least one endonuclease and DNA binding moiety are joined by a linker including two, three, four, five, six, seven, eight, nine, ten or more amino acids. In other embodiments, some configurations of Cas9-endonuclease and donor DNA binding moieties are: direct fusion, association (multimerization domains like leucine zippers, fkbp/FRB, etc.), engineered association via antibody mimetics, or any synthetic macromolecule (carbohydrate-, protein-, or lipid-based) which bind to Cas9 endonuclease and also bind to the donor DNA in a sequence specific manner. In other embodiments, the fusion protein further includes a nuclear localization signal (NLS), such as SV40 NLS. In other embodiments, the CRISPR protein is a *Streptococcus pyogenes*-derived cas protein. In other embodiments, the CRISPR protein is not a *Streptococcus pyogenes*-derived cas protein. In various embodiments, CRISPR protein is cpf1, such as AsCpf1 from Acidaminococcus and LbCpf1 is from Lachnospiraceae. In other embodiments, the CRISPR protein is cas9. In other embodiments, the CRISPR protein is cpf1. In other embodiments, the fusion protein includes a reporter protein. In various embodiments, the report protein includes a fluorescent labeled protein including green or red fluorescent protein (GFP or RFP, including enhanced eGFP), mCherry, or similar proteins. In other embodiments, the vector is a DNA vector, plasmid, artificial chromosome. In other embodiments, the vector is a virus, such as adenovirus, adeno associated virus, or lentivirus.

In other embodiments, the vector encodes one or more guide RNAs (gRNAs), wherein the one or more gRNAs include a sequence capable of binding to a protospacer adjacent motif (PAM). In other embodiments, the one or more gRNAs include a sequence capable of binding to a PAM. In other embodiments, the PAM includes the sequence NGG. In other embodiments, the PAM includes the sequence NAG. In other embodiments, the gRNA comprise a CRISPR-derived RNAs (crRNA) and trans-acting antisense RNA (tracRNA). In various embodiments, the gRNA is 10, 20, 30, or 40 or more nucleotides in length. In various embodiments, about 15, 16, 17, 18, 19, 20, 21, 22, 23, 24, 25 or more nucleotides are cognate to a gene of interest. In various embodiments, about 20 nucleotides are cognate to a genetic loci of interest. For example, this includes gRNA designs that hybridize to a target sequence with $N_{20}NGG$. In some embodiments, the CRISPR protein is cas9. In other embodiments, the CRISPR protein is cpf1. In various embodiments, the composition is used in a method for altering a target polynucleotide sequence in a cell including contacting the polynucleotide sequence with a CRISPR protein (e.g., cas9) with at least one gRNA directing CRISPR to hybridize to a cognate sequence on a target polynucleotide sequence, wherein the target polynucleotide sequence is cleaved, and wherein the efficiency of alteration of cells that express CRISPR protein is from about 10-20%, 30-40%, 40-50%, or 50-80% or more. In various embodiments, the efficiency of alteration is improved 1×, 2, 3×, 4×, 5×, 6×, 7×, 8×, 9×, 10×, 20×, 30×, 40×, 50×, 100× when compared to a method using a native wild-type endonuclease. Further described herein is a quantity of cells produced using the described method.

Further described is a method of genomic editing including providing a quantity of one or more vectors each encoding a fusion protein including at least one endonuclease and a DNA binding moiety and contacting a population of cells with the quantity of the one or more vectors. In various embodiments, the fusion protein endonuclease includes at least one endonuclease selected from the group consisting of: cas regularly interspaced short palindromic (CRISPR) protein, a zinc finger nuclease (ZFNs) or transcription activator-like effector nucleases (TALENs). In other embodiments, the DNA binding moiety includes a zinc finger protein. In other embodiments, the fusion protein includes at least one endonuclease CRISPR protein and a DNA binding moiety zinc finger protein. In other embodiments, the zinc finger protein includes a left handed, right handed, or both zinc fingers. In other embodiments, the zinc finger includes a left handed CCR5 sequence. In other embodiments, DNA binding moieties can include specific domains or full-length proteins in their entirety, including transcription factors, endonucleases, zinc fingers, TALENs, endonuclease-minus Cas-9+guide strand RNA, or other such ribonucleoprotein that can bind directly or indirectly to specific DNA sequences. In other embodiments, the at least one endonuclease and DNA binding moiety are joined by a linker including two, three, four, five, six, seven, eight, nine, ten or more amino acids. In other embodiments, Some, configurations of Cas9-endonuclease and donor DNA binding moieties are: direct fusion, association (multimerization domains like leucine zippers, fkbp/FRB, etc.), engineered association via antibody mimetics, or any synthetic macromolecule (carbohydrate-, protein-, or lipid-based) which bind to Cas9 endonuclease and also bind to the donor DNA in a sequence specific manner. In other embodiments, the fusion protein further includes a nuclear localization signal (NLS), such as SV40 NLS. In other embodiments, the CRISPR protein is a *Streptococcus pyogenes*-derived cas protein. In other embodiments, the CRISPR protein is not a *Streptococcus pyogenes*-derived cas protein. In various embodiments, CRISPR protein cpf1, such as AsCpf1 from Acidaminococcus and LbCpf1 is from Lachnospiraceae. In other embodiments, the CRISPR protein is cas9. In other embodiments, the CRISPR protein is cpf1. In other embodiments, the fusion protein includes a reporter protein. In various embodiments, the report protein includes a fluorescent labeled protein including green or red fluorescent protein (GFP or RFP, including enhanced eGFP), mCherry, or similar proteins. In other embodiments, the method is an in vivo method. In other embodiments, the method is an in vitro method. In certain embodiments, the population of cells include embryonic stem cells, including human or mouse embryonic stem cells. In various embodiments, the method includes generation of a double stranded break (DSB) in the quantity of cells, wherein homologous recombination (HR) of the DSB results in editing of the genome of the cells. In other embodiments, HR includes non-homologous end joining (NHEJ) introducing missense or nonsense of a protein expressed at the locus. In other embodiments, the missense or nonsense results in a knock-out of a target sequence in the genome. In other embodiments, HR includes homology directed repair (HDR) introduces template DNA. In other embodiments, the HDR results in a knock-in of a target sequence in the genome. In other embodiments, the template DNA is cognate to a target sequence. In other embodiments, the template DNA is cognate to a wild-type genetic sequence. In other embodiments, the template DNA contains an expression cassette, for example, including a sequence transcribed and translated into a protein of interest. In other embodiments, the template DNA includes at least 80 bases of exact sequence homology both upstream and downstream of about 20 bases cognate to a target sequence, or cognate to a wild-type genetic sequence. In other embodiments, the upstream and downstream sequences are at least 10, 20, 30, 40, 50, 60, 70, 80, 90, 100, 110, 120, 130, 140, 150, 200, 250, 300, 350, 400, 450, 500 or more base pairs. In other embodiments, the template DNA includes a sequence for binding of a DNA binding moiety. In other embodiments, the template DNA includes about 12 base pairs constituting the left-handed CCR5-zinc finger-binding site. In other embodiments, contacting a population of cells with the quantity of the one or more vectors include transfection, electroporation, and/or lipofection. In other embodiments, the vector is a DNA vector, plasmid, artificial chromosome. In other embodiments, the vector is a virus, such as adenovirus, adeno associated virus, or lentivirus.

In other embodiments, the vector encodes one or more guide RNAs (gRNAs), wherein the one or more gRNAs include a sequence capable of binding to a protospacer adjacent motif (PAM). In other embodiments, one or more exogenous gRNAs are introduced to the quantity of cells. In other embodiments, the one or more gRNAs include a sequence capable of binding to a PAM. In other embodiments, the PAM includes the sequence NGG. In other embodiments, the PAM includes the sequence NAG. In other embodiments, the gRNA comprise a CRISPR-derived RNAs (crRNA) and trans-acting antisense RNA (tracRNA). In various embodiments, the gRNA is 10, 20, 30, or 40 or more nucleotides in length. In various embodiments, about 15, 16, 17, 18, 19, 20, 21, 22, 23, 24, 25 or more nucleotides are cognate to a gene of interest. In various embodiments, about 20 nucleotides are cognate to a genetic loci of interest. For example, this includes gRNA designs that hybridize to a target sequence with $N_{20}NGG$. In some embodiments, the CRISPR protein is cas9. In various embodiments, the composition is used in a method for altering a target polynucleotide sequence in a cell including contacting the polynucleotide sequence with a CRISPR protein (e.g., cas9) with at least one gRNA directing CRISPR to hybridize to a cognate sequence on a target polynucleotide sequence, wherein the target polynucleotide sequence is cleaved, and wherein the efficiency of alteration of cells that express CRISPR protein is from about 10-20%, 30-40%, 40-50%, or 50-80% or more. In various embodiments, the efficiency of alteration is improved 1×, 2, 3×, 4×, 5×, 6×, 7×, 8×, 9×, 10×, 20×, 30×, 40×, 50×, 100× when compared to a method using a native wild-type endonuclease. Further described herein is a quantity of cells produced using the described method.

For example, the method of genomic editing including providing a quantity of one or more vectors each encoding a fusion protein including at least one endonuclease and a DNA binding moiety and contacting a population of cells with the quantity of the one or more vectors, wherein the at least one endonuclease includes a CRISPR protein and a DNA binding moiety includes zinc finger protein, contacting a population of cells with the quantity of the one or more vectors includes transfection, electroporation, and/or lipofection, further including gRNA and/or template DNA, and after contacting a population of cells, results in generation of a double stranded break (DSB) and homology directed repair (HDR) introduces the template DNA in the genome of the population of cells. In other embodiments, the template DNA is cognate to a target sequence. In other embodiments, the template DNA is cognate to a wild-type genetic sequence. In other embodiments, the template DNA contains an expression cassette, for example, including a sequence transcribed and translated into a protein of interest. In other embodiments, the template DNA includes at least 80 bases of exact sequence homology both upstream and downstream of about 20 bases cognate to a target sequence, or cognate to a wild-type genetic sequence. In other embodiments, the template DNA includes a sequence for binding of a DNA binding moiety. In other embodiments, the template DNA includes about 12 base pairs constituting the left-handed CCR5-zinc finger-binding site.

Also described is a kit for genomic editing including a quantity of one or more vectors each encoding a fusion protein including at least one endonuclease and a DNA binding moiety and contacting a population of cells with the quantity of the one or more vectors, and further including a template DNA cognate to a target sequence or a wild-type genetic sequence, the template DNA including at least 10 bases of exact sequence homology both upstream and downstream of about 20 bases cognate to a target sequence, or cognate to a wild-type genetic sequence. In other embodiments, the DNA binding moiety includes a zinc finger protein. In other embodiments, the fusion protein includes at least one endonuclease CRISPR protein and a DNA binding moiety zinc finger protein. In other embodiments, the kit includes one or more guide RNAs (gRNAs), wherein the one or more gRNAs include a sequence capable of binding to a protospacer adjacent motif (PAM).

In other embodiments, the upstream and downstream sequences are at least 10, 20, 30, 40, 50, 60, 70, 80, 90, 100, 110, 120, 130, 140, 150, 200, 250, 300, 350, 400, 450, 500 or more base pairs. In various embodiments, the fusion protein endonuclease includes at least one endonuclease selected from the group consisting of: cas regularly interspaced short palindromic (CRISPR) protein, a zinc finger nuclease (ZFNs) or transcription activator-like effector nucleases (TALENs). In other embodiments, the DNA binding moiety includes a zinc finger protein. In other embodiments, the fusion protein includes at least one endonuclease CRISPR protein and a DNA binding moiety zinc finger protein. In other embodiments, the zinc finger protein includes a left handed, right handed, or both zinc fingers. In other embodiments, the zinc finger includes a left handed CCR5 sequence. In other embodiments, DNA binding moieties can include specific domains or full-length proteins in their entirety, including transcription factors, endonucleases, zinc fingers, TALENs, endonuclease-minus Cas-9+guide strand RNA, or other such ribonucleoprotein that can bind directly or indirectly to specific DNA sequences. In other embodiments, the at least one endonuclease and DNA binding moiety are joined by a linker including two, three, four, five, six, seven, eight, nine, ten or more amino acids. In other embodiments, some, configurations of Cas9-endonuclease and donor DNA binding moieties are: direct fusion, association (multimerization domains like leucine zippers, fkbp/FRB, etc.), engineered association via antibody mimetics, or any synthetic macromolecule (carbohydrate-, protein-, or lipid-based) which bind to Cas9 endonuclease and also bind to the donor DNA in a sequence specific manner. In other embodiments, the fusion protein further includes a nuclear localization signal (NLS), such as SV40 NLS. In other embodiments, the CRISPR protein is a *Streptococcus pyogenes*-derived cas protein. In other embodiments, the CRISPR protein is not a *Streptococcus pyogenes*-derived cas protein. In various embodiments, CRISPR protein is cpf1, such as AsCpf1 from Acidaminococcus and LbCpf1 is from Lachnospiraceae. In other embodiments, the CRISPR protein is cas9. In other embodiments, the fusion protein includes a reporter protein. In various embodiments, the report protein includes a fluorescent labeled protein including green or red fluorescent protein (GFP or RFP, including enhanced eGFP), mCherry, or similar proteins. In various embodiments, the kit is capable of generating a double stranded break (DSB) in the quantity of cells, wherein homologous recombination (HR) of the DSB results in editing of the genome of the cells. In other embodiments, HR includes non-homologous end joining (NHEJ) introducing missense or nonsense of a protein expressed at the locus. In other embodiments, the missense or nonsense results in a knockout of a target sequence in the genome. In other embodiments, HR includes homology directed repair (HDR) introduces template DNA. In other embodiments, the HDR results in a knock-in of a target sequence in the genome. In other embodiments, the template DNA is cognate to a target sequence. In other embodiments, the template DNA is cognate to a wild-type genetic sequence. In other embodiments, the template DNA contains an expression cassette, for example, including a sequence transcribed and translated into a protein of interest. In other embodiments, the template DNA includes at least 80 bases of exact sequence homology both upstream and downstream of about 20 bases cognate to a target sequence, or cognate to a wild-type genetic sequence. In other embodiments, the upstream and downstream sequences are at least 10, 20, 30, 40, 50, 60, 70, 80, 90, 100, 110, 120, 130, 140, 150, 200, 250, 300, 350, 400, 450, 500 or more base pairs. In other embodiments, the template DNA includes a sequence for binding of a DNA binding moiety. In other embodiments, the template DNA includes about 12 base pairs constituting the left-handed CCR5-zinc finger-binding site. In other embodiments, contacting a population of cells with the quantity of the one or more vectors include transfection, electroporation, and/or lipofection. In other embodiments, the vector is a DNA vector, plasmid, artificial chromosome. In other embodiments, the vector is a virus, such as adenovirus, adeno associated virus, or lentivirus.

In other embodiments, the vector encodes one or more gRNAs, wherein the one or more gRNAs include a sequence capable of binding to a PAM. In other embodiments, one or more exogenous gRNAs are introduced to the quantity of cells. In other embodiments, the one or more gRNAs include a sequence capable of binding to a PAM. In other embodiments, the PAM includes the sequence NGG. In other embodiments, the PAM includes the sequence NAG. In other embodiments, the gRNA comprise a CRISPR-derived RNAs (crRNA) and trans-acting antisense RNA (tracRNA). In various embodiments, the gRNA is 10, 20, 30, or 40 or more nucleotides in length. In various embodiments, about 15, 16, 17, 18, 19, 20, 21, 22, 23, 24, 25 or more nucleotides are cognate to a gene of interest. In various embodiments, about 20 nucleotides are cognate to a genetic loci of interest. For example, this includes gRNA designs that hybridize to a target sequence with $N_{20}NGG$. In some embodiments, the CRISPR protein is cas9. In other embodiments, the CRISPR protein is cpf1. In various embodiments, the kit is used in a method for altering a target polynucleotide sequence in a cell including contacting the polynucleotide sequence with a CRISPR protein (e.g., cas9) with at least one gRNA directing CRISPR to hybridize to a cognate sequence on a target polynucleotide sequence, wherein the target polynucleotide sequence is cleaved, and wherein the efficiency of alteration of cells that express CRISPR protein is from about 10-20%, 30-40%, 40-50%, or 50-80% or more. In various embodiments, the efficiency of alteration is improved 1×, 2, 3×, 4×, 5×, 6×, 7×, 8×, 9×, 10×, 20×, 30×, 40×, 50×, 100× when compared to a method using a native wild-type endonuclease. Further described herein is a quantity of cells produced using the described method.

Also described herein is a method of multi-locus genomic editing including inducing sticky end formation at one or more loci by adding a CRISPR protein, providing a quantity of one or more guide strand RNAs, ligating one or more single-stranded donor DNA, hybridizing one or more double-stranded DNA with a terminating oligonucleotide, synthesis of one or more double stranded DNA from the one or more single-stranded donor DNA to the one or more double-stranded DNA completing the donor DNA strand to form a sticky end, and joining compatible sticky ends at one or more loci. In various embodiments, providing a quantity of one or more guide strand RNAs includes T7 RNA synthesis of guide-strand RNA. In other embodiments, ligating one or more single-stranded donor DNA includes splint mediated ligation of single-stranded donor DNA sequence onto the 5' end of the guide-strand RNA. In various embodiments, the 5' nucleotide of the synthesized donor DNA has an exonuclease resistant phosphorothioate bond with its neighboring nucleotide. In other embodiments, hybridization of double-stranded DNA terminating oligonucleotide occurs. In other embodiments, synthesis of one or more double stranded DNA from the one or more single-stranded donor DNA to the one or more double-stranded DNA completing the donor DNA strand includes isothermal DNA polymerase (Klenow exo-) reaction. In other embodiments, synthesis of one or more double stranded DNA from the one or more single-stranded donor DNA to the one or more double-stranded DNA completing the donor DNA strand to form a sticky end is by T4-DNA ligase reaction. In various embodiments, complete integration happens upon ligation of the sticky end of the donor DNA and homologous recombination between donor and genomic DNA due to their proximity and sequence homology. In various embodiments, the PAM is TTTN. In various embodiments, the cpf1 sticky end is 19 bp after the PAM on the targeted+strand, and 23 bp on the opposite strand with a 5' overhang. In various embodiments, cpf1 such as AsCpf1 from Acidaminococcus and LbCpf1 is from Lachnospiraceae.

Example 1

Experimental Design

As described, gene manipulation by Cas-9 includes genetic knockouts through Cas-9 DNA cleavage and emergency DNA repair systems are relatively easy to produce, yet gene knock-ins/fusions are much more challenging because: of larger DNA inserts (GFP=717 base pairs) integrate with low efficiency, dependency of integration rate is dependent on insert DNA concentration, higher concentrations of linear DNA is toxic to cells.

Through actively recruiting the linear DNA insert in closer proximity to the genomic cleavage site, one can increase integration efficiency of large DNA fragments into the genome, be able to use lower linear DNA concentrations without sacrificing efficiency, and quickly screen through various protein configurations due to cell culture system. A nice biological (fluorescent) readout allows for quick optimization.

To aid development of a quick and easy analysis of CRISPR/Cas9 optimization, a GFP:B-actin reporter system is developed including Step 1) Building Cas9:CCR5:NLS-fusion protein; Step 2) Synthesize sgRNA against human genomic B-actin; Step 3) Design suitable linear GFP DNA sequence optimized for efficient DNA repair, Step 4) Screen for green cells and optimize if needed.

Example 2

Study Model

GFP-βactin is our first genomic GFP-tagged goal protein for the following reasons: it expresses constantly and one can screen cells quickly, any frame shift and/or cleavage leading to knocking out actin results in cell death. The two fluorescent labels, mCherry and GFP, are the means of screening integration efficiency and cell viability. GFP can only express if it is integrated into the genome and is in-frame with surrounding sequence. The mCherry should express in all living transfected cells.

The experimental conditions included: 1) mCherry only (transfection efficiency/cell viability control); 2) Cas-9-nls, sgRNA, donor DNA, mCherry (NHEJ efficiency); 3) Donor DNA, sgRNA, mCherry (cell viability due to linear DNA); 4) Cas-9-ZF, donor DNA, mCherry (off-target CCR5 effects); 5) Cas-9-ZF, sgRNA, donor DNA, mCherry (test).

Fluorescently labeled GFP signal allows rapid determination of cell viability due to the constituent reagents in the transfection in order to optimize future electroporations. GFP signal will only come from cells positive for integration and colonies can be isolated, collected, expanded, genotyped to determine GFP insertion sites, and imaged to determine proper protein localization.

Example 3

Methods

A vector was purchased from Addgene encoding Cas-9-NLS (Plasmid #42251). The C-terminal NLS was removed from the 3' end of the DNA sequence and replaced with the coding sequence for a short 3× glycine-serine linker (6 amino acids total), the left-handed CCR5, and the NLS previously removed was added back. The vector was linearized and used as template for a T7 MMESSAGE® capped mRNA synthesis kit. The RNA is cleaned up using an RNeasy kit followed by phenol/chloroform extraction and ethanol precipitation.

Guide-strand RNA is synthesized using the following protocol. A GFP-gene fusion (GFP-βactin) was published as a functionally viable protein and therefore became the desired genomic GFP-tagged endogenous protein. PCR primers were designed to amplify sequence surrounding this region for targeted insertion within the HEK293 cell line and the PCR product was sequenced to confirm accuracy of the published chromosomal sequence data. 20 bases of sequence within the genome are chosen as the hybridization target for the guide-strand RNA and run through several algorithms on-line to both maximize guide-strand hybridization to the genome and to minimize off-target hybridizations. After a sequence is selected, a 120 bp DNA template is assembled by Klenow fill-in and PCR amplification from 4 ssDNA oligo nucleotides ordered from IDT, only one of which is unique to each guide-strand (i.e. only one oligo, $18, must be purchased for a unique sgRNA). The template consists of a T7 promoter, 20 bases of unique homology to the genomic target, and 80 bases that will encode the Cas9-binding hairpins. The recipe is as follows: 5 pmoles DNA template, 125 uM NTP mix, transcription buffer (HEPES-$MgCl_2$, DTT, spermidine, pH 7.5), 150 ug T7 RNA pol (20 ul, made in house) in a total volume of 200 ul. The reaction is incubated at 37° C. for 2-4 hours until a white precipitate of $Mg^{2+}$ (pyrophosphate) collects at the bottom of the tube. 25 ul of 0.5M EDTA is added to clear the precipitate and halt further polymerization. The newly synthesized RNA is run out on an 8% acrylamide Urea-PAGE gel to separate unincorporated NTPs, truncated RNAs, and DNA template from the full-length 100base sgRNA. The RNA is visualized via shadow imaging over a TLC plate, the bands are cut out from the gel and eluted from the gel by electrophoresis on a Whatman elutrap. The RNA is then ethanol precipitated and dissolved in 10 mM Tris pH 8.0 to the desired concentration.

After some test integrations, it was determined that the donor DNA sequence should consist of at least 80 bases of exact sequence homology both upstream and downstream of the 20 bases required by Cas-9 to cause the double stranded DNA break. These 80 bp up- and 80 bp downstream are engineered on the 5' and 3' ends of the donor DNA sequence that are to be added into the genome. It is significant to note that the sequencing data used to determine the optimal sgRNA hybridization sequence is also useful to generate the precise homology arms. The 12 base pairs constituting the left-handed CCR5-zinc finger-binding site are added strategically as to not interfere with either the final coding sequence or splicing of the mRNA transcribed from the target locus. Super-folder GFP (sfGFP), mCerulean, and tagRFP were codon optimized, through silent mutations, such that any consensus mRNA splice donor and splice acceptor sequences were removed from both sense and antisense strands. The βactin homology domains and CCR5-binding site were extended in both directions from sfGFP in PCR reactions. The linear DNA was purified from an LMP agarose gel, extracted using a Qiagen Gel Extraction Kit, phenol/chloroform extracted, ethanol precipitated, and dissolved in TE buffer (10 mM Tris, 1 mM EDTA, pH 8.0) to the desired concentration.

Because of the mixed nature of the various components (100base sgRNA, 4500base Cas-9-ZF mRNA, 6500 bp Ubi6::mCherry plasmid as transfection control, 890 bp linear donor DNA) going into the transfection, it was determined that electroporation was the delivery method of choice as opposed to lipophilic or receptor mediated transfection reagents. $1 \times 10^6$ cells are suspended in 1×PBS containing: 2 ug sgRNA, 1.5 ug Cas-9-ZF mRNA, 50 ng donor DNA, and 1 ug plasmid DNA in 40 ul total volume. The cells are electroporated in a square wave, 42V, 50 ms, pulse supplied by Harvard Apparatus BTX-840. The cells are then plated on 60 mm glass bottom cell culture dishes for ease of imaging, analysis, and clonal harvesting. HEK293 cells are grown in DMEM with 5% FBS and gentamicin. The CRISPR/Cas mRNA or protein, sgRNA, and donor DNA mixture is injected into zebrafish embryos at 10-30 minutes post fertilization to make our zebrafish transgenic lines.

Example 4

Preliminary Results

Figure 2:
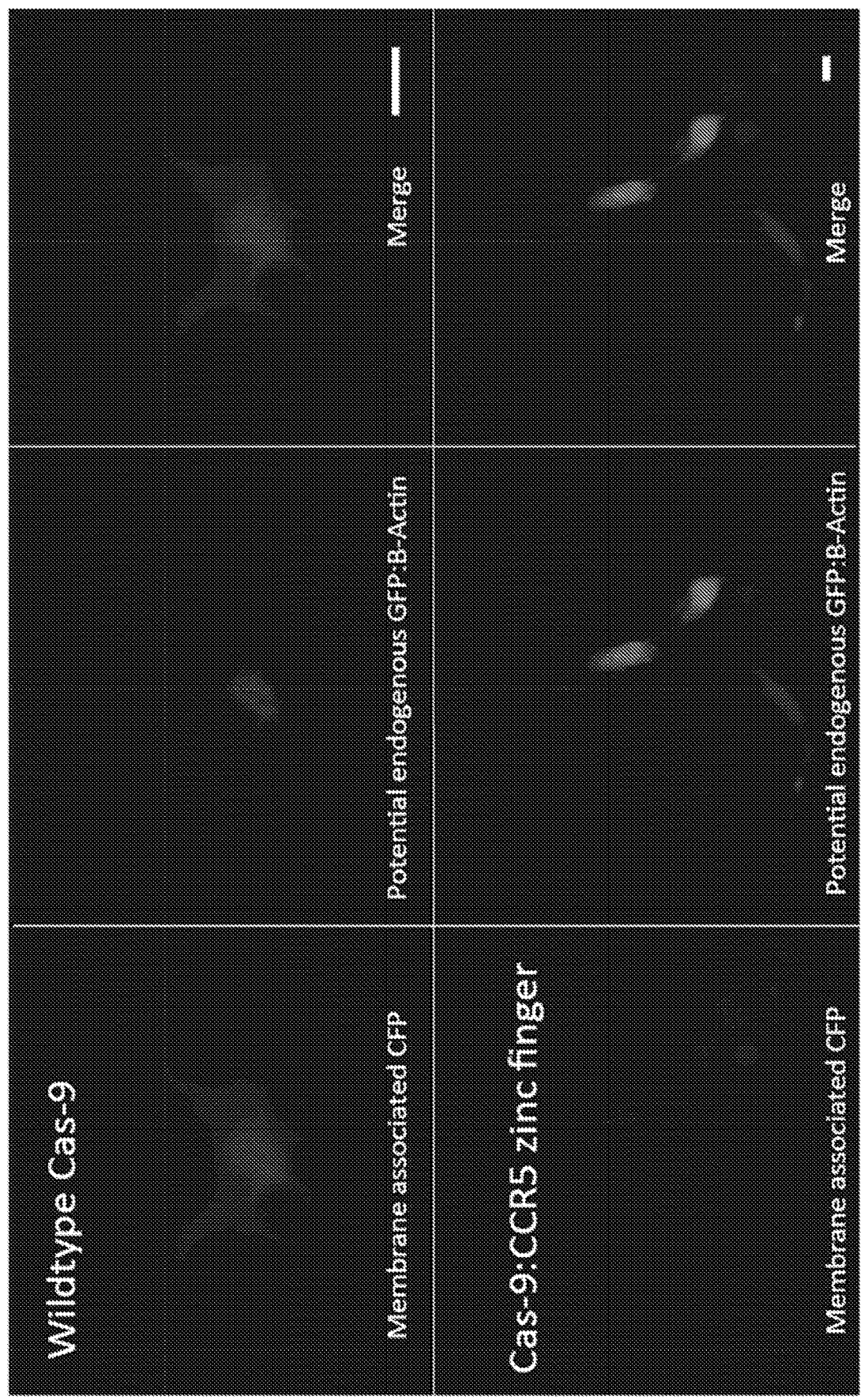
FIG. 2. Comparison between wildtype Cas-9 and recombinant Cas-9 using GFP as reporter and beta-actin as the target gene. Wild-type condition included 5 out of 18 CFP positive colonies that were also GFP positive, 2 of which were only GFP positive (i.e., stable integrants). Under Cas-9 zinc finger conditions included 9 out of 12 CFP positive colonies that were also GFP positive, 4 of which were only GFP positive. Scale bars=10 μM.
Figures 3, 3A:
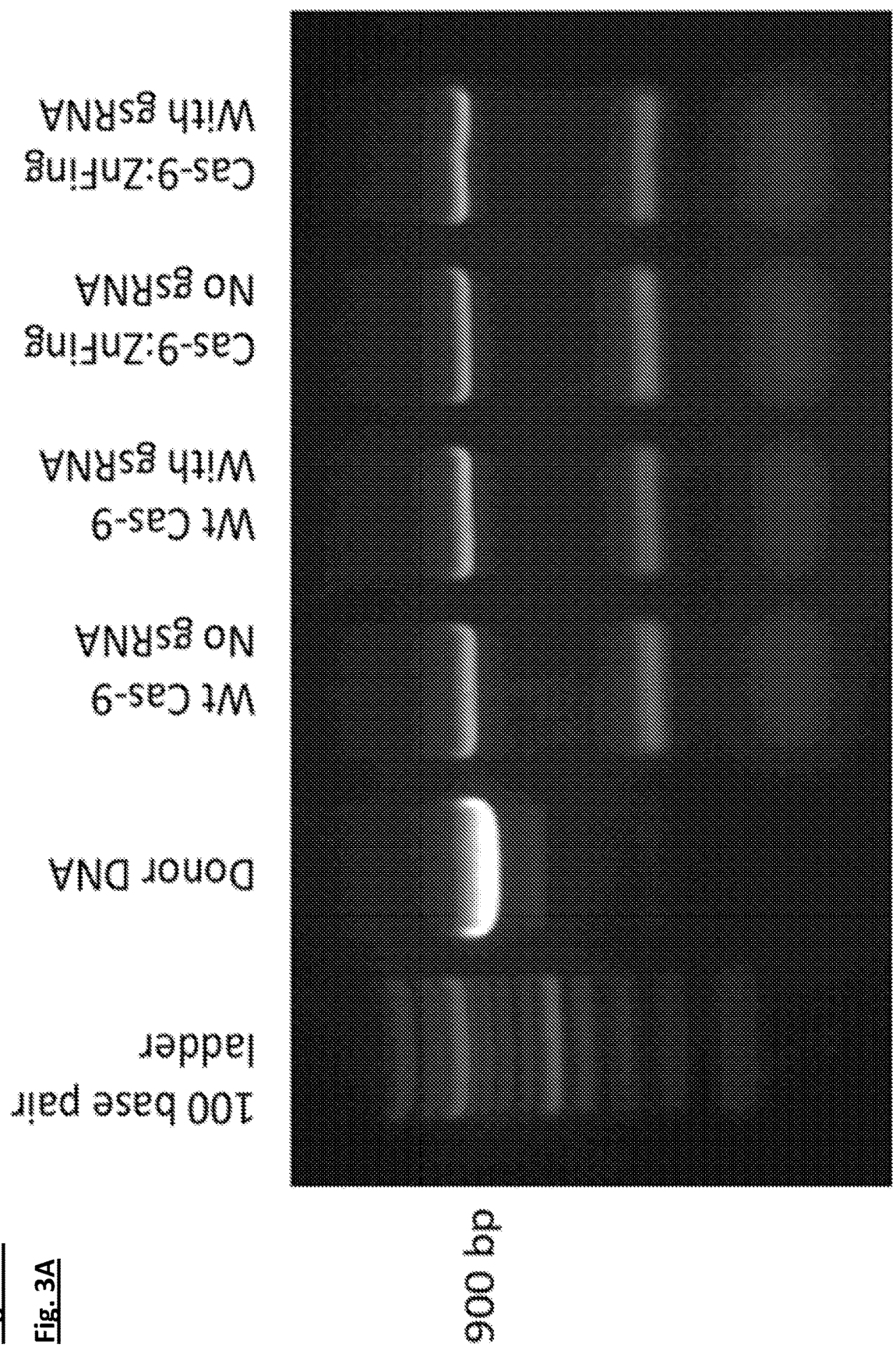
FIG. 3.
(FIG. 3A) Data showing that the addition of the Zinc-finger to Cas9 does not confer additional zinc-finger dependent endonuclease activity. Donor DNA (900 bp) contains the CCR5 DNA binding sequence (base pairs 80-92 on the 5' end of the linear DNA). Combinations of protein and guide strand are labeled for each condition.
Figure 3B:
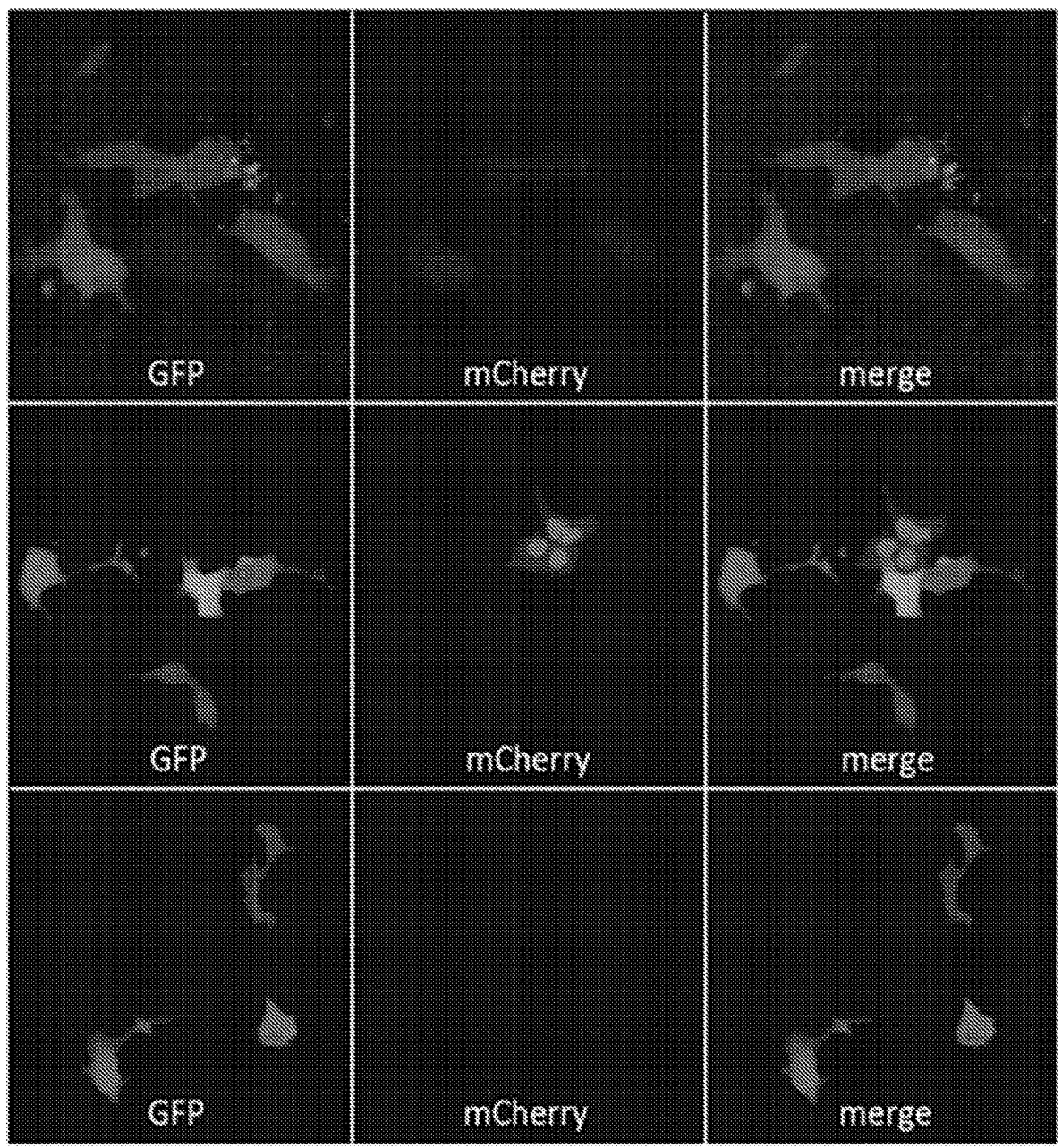
(FIG. 3B) Three examples of GFP signal due to integration of donor DNA. The GFP positive clones are being validated. mCherry is the internal viability control.
Figure 4:
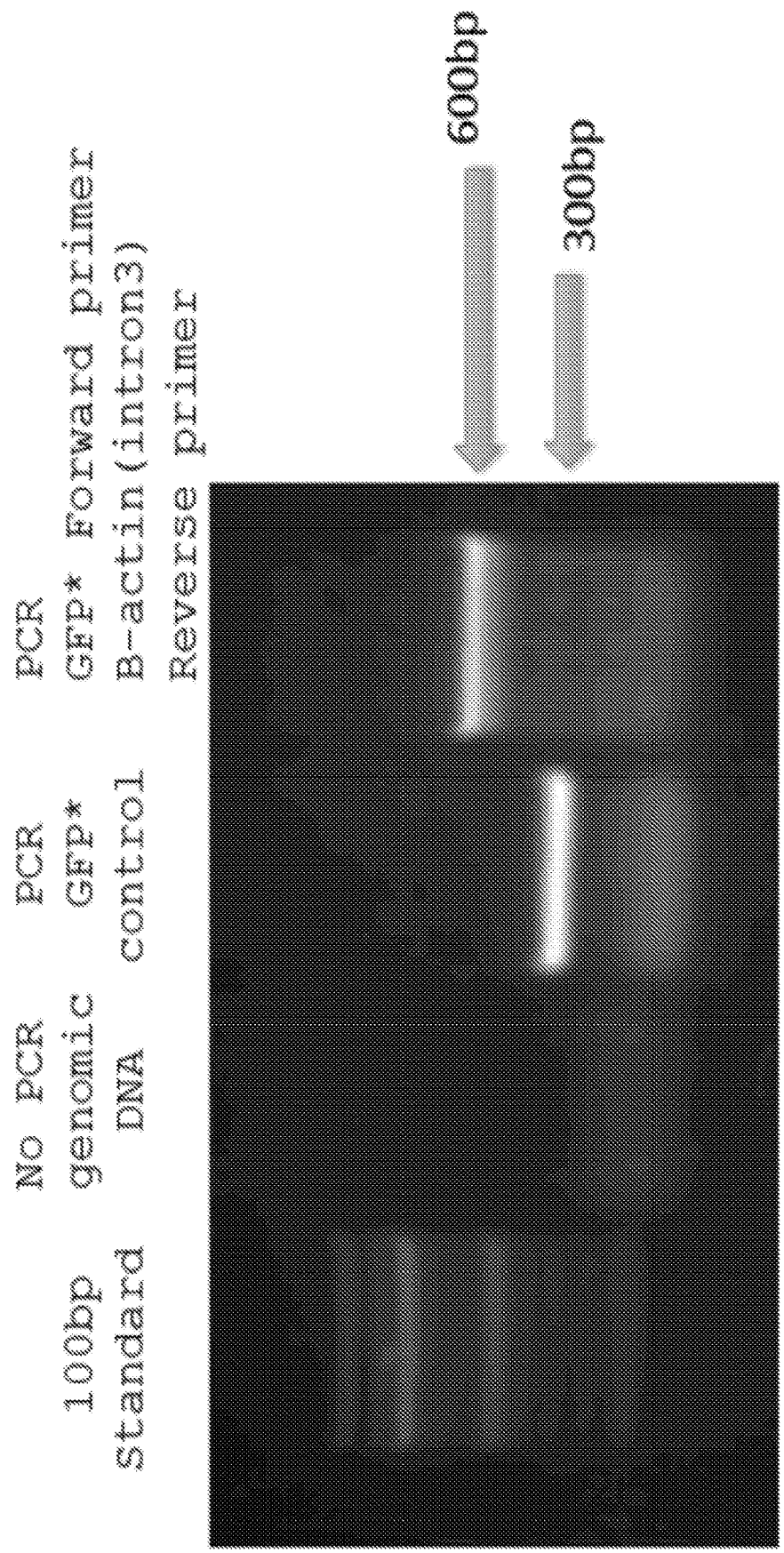
FIG. 4: Integration of GFP in beta-actin validated by PCR. PCR of GFP is a 300 bp fragment of the total GFP sequence, beta-actin reverse primer anneals 300 bp downstream of the sfGFP integration site.

As shown in FIG. 2, a wild-type condition resulted in only 5 out of 18 CFP positive colonies that were also GFP positive, 2 of which were only GFP positive (i.e., stable integrants). By contrast, using the describe Cas-9 zinc finger suste, 9 out of 12 CFP positive colonies that were also GFP positive, 4 of which were only GFP positive. In FIG. 3, results demonstrate that addition of the Zinc-finger to Cas9 does not confer additional zinc-finger dependent endonuclease activity (FIG. 3A) and three examples of GFP signal due to integration of donor DNA are shown (FIG. 3B). The GFP positive clones are being validated (FIG. 4). mCherry is the internal viability control. This work was done in HEK-293t cells to generate GFP fused to endogenous beta actin.

This proof-of concept of labeling endogenous proteins in stem cells can readily be translated to generate transgenic animals quickly. The ability to recruit donor DNA, via the Cas-9:CCR5 zinc finger, to the break site of Cas-9 increases the integration of foreign DNA (723 base pairs, GFP) 2.7 fold over wildtype Cas-9 in this first iteration. By adding more genomic sequence on either side of the donor DNA one should be able to get higher integration efficiencies.

Example 5

Subsequent Projects and Applications

Once proper conditions for integration are worked out, one can genetically tag Oct4 with tagRFP, Sox2 with CFP, and Nanog with sfGFP in separate mouse ES cell lines, and combine them in all possible permutations. These cell lines will be useful in their own right but are useful to generate transgenic mouse lines where we are able to visualize absolute amounts and localizations of these developmentally important proteins expressed as endogenous levels of fusion proteins.

Additionally, one can skip in vivo translation of Cas-9 mutant by bacterial expression and subsequently purify Cas-9 fusion protein. This purified protein would be pre-mixed and equilibrated with both guide strand RNA and donor DNA necessary for all unique genomic integrations. These preassembled endonuclease/donor DNA integration units could be injected or transfected into embryos or any cell line. This configuration allows not only genomic editing at the earliest stages but also would allow multiple integration events simultaneously with high efficiency. Such would be the first successful generation of a mouse ES stem cell line with all three of the previously described integrations, simultaneously, as the first multiple knock-in lines. In other examples, one could also target RNA probes such as Spinach (1 or 2) into the genome to get visual read outs of nascent transcription and/or mRNA splicing events.

Example 6

Construct Formats

Additionally, one could potentially combine all of the elements of this CRISPR, Cas-9:fusion, donor DNA-targeting system into a single virus. The attenuated virus would express Cas-9:fusion, and guide strand RNA under an orthogonally induced promoter (i.e. ecdysone receptor-driven expression would work in all species except insect) or cell type-specific promoter, and the viral genome would contain the donor DNA sequence flanked on both sides by the 20 base pairs recognized by the guide strand RNA. This configuration would generate linear donor DNA with the requisite flanking homology sequence to the genomic target and would be recruited by Cas-9:fusion-sgRNA endonuclease to the target locus. This viral construct could be used to: correct genetic mutations, make drugable targets more sensitive to drugs, or make previously non-drugable targets drugable, and would self-destruct in the process.

Example 7

Exemplary Sequences Used in Applications

A variety of constructs were prepared to test the variable designs described herein. In on example, a Cas-9 zinc-finger fusion protein was generated, including the following elements: the Cas-9 endonuclease, a short 9 amino acid linker (ssagagaga, SEQ ID NO:9), left-handed CCR5 zinc-finger, 4 amino acids (wrlp, SEQ ID NO:10), and a nuclear localization sequence, stop. Nucleotide sequence is described in SEQ ID NO:1 and amino acid sequence of the construct is described in SEQ ID NO:2. For Ni-NTA purification of the Cas-9 fusion protein, the Inventors added a 6× histidine tag to the extreme carboxy-terminal end of the protein.

Other donor DNA sequence examples used or synthesized include a super-folder GFP: Beta-actin (SEQ ID NO:3) utilized in the human cancer cell line HEK293. This sequence includes 80 base pairs of sequence homology upstream of the Cas-9 endonuclease cleavage site, left-handed CCR5 binding sequence, 12 bases encoding a short linker, super-folder GFP, and 80 base pairs of sequence homology downstream of the endonuclease cleavage site.

Another example includes a Sox-2:PS-mOrange2:Spinach2 SEQ ID NO:4 for use in zebrafish (*D. rerio*). 81 base pairs of sequence homology upstream of the Cas-9 endonuclease cleavage site, silent mutations to the Sox-2 carboxy-terminal end, 48 bases coding for 16 glycine/serine residues, photoswitchable orange fluorescent protein (PS-mOrange2), 144 base pairs non-coding, left-handed CCR5 binding sequence, Spinach-2 (mRNA fluorescent reporter), and 82 base pairs of sequence homology downstream of the endonuclease cleavage site.

Additional example includes Oct-4:GFP (SEQ ID NO:5) for use in mouse (*M. musculus*). This sequence includes 82 base pairs of sequence homology upstream of the Cas-9 endonuclease cleavage site, 27 bases encoding a glycine/alanine linker, super-folder GFP, left-handed CCR5 binding sequence, and 94 base pairs of sequence homology downstream of the endonuclease cleavage site.

Finally, a variety of guide-strand RNA sequences were utilized including human beta-Actin (SEQ ID NO:6), zebrafish Sox-2 (SEQ ID NO:7), and mouse Oct-4 (SEQ ID NO:8).

Example 8

Experimental Protocol

An exemplary experimental protocols for applying the above constructs is described further herein:
All cas9 protein/sgRNA/donor DNA complexes are allowed to equilibrate at room temp for 30 minutes.
Human B-actin sgRNA and donor DNA can used
A "1:2:3" mixture strategy is utilized (e.g. 1 pmol plasmid: 2 pmol sgRNA: 3 pmol protein: 3 pmol of sgRNA) with 90 ng (0.013 pmol) plasmid DNA. These conditions are optimized for minimal protein usage and for clear read-out on the gel.
Cas9 reactions are carried out at 28 degrees ° C. for two hours.
XmaI digest (single cut) is utilized, two hour reaction at 37 degrees C.
Samples were cleaned up with qiagen PCR clean-up reagents/columns prior to gel electrophoresis.
Samples were run on a 1% agarose gel in TAE.

The above protocol demonstrates that Cas9-zinc finger fusion protein linearizes plasmid DNA efficiently (FIG. 5). It appears that some off-target cleavage may occur due to the presence of the zinc finger. However, off-target cleavage is ameliorated when donor DNA is included. The above approach has allowed for optimized conditions for injections into zebrafish, as well as in vitro confirmation that the B-actin guide strand and cas-9 fusion are functional together. Further confirmation is available based on running flow cytometry cell sorting (FACS) on frozen GFP:B-actin HEK cells. Once a GFP sorted culture is prepared, genomic analysis can confirm editing.

Example 9

All-In-One CRISPR Editing

In an alternative embodiment, mixtures of specific guides strand RNA-donor DNA hybrids could allow for parallel, multi-locus mutations. More specifically, mixtures of specific guide strand RNA-donor DNA hybrids and a single CRISPR protein preparation are deployed. This approach would allow a researcher to make simultaneous additions/mutations to multiple loci in the genome of any organism or cell line.

By using Cpf1 instead of Cas9 for CRISPR genome editing, this allows one to take advantage of highly efficient sticky-end donor DNA-genomic DNA ligation repairs. A partial unnatural nucleotide backbone in the donor DNA assembly primers make the sticky-end of the donor DNA less vulnerable to degradation, which preservation theoretically will allow for much higher ligation efficiencies.

Parallel, multi-locus, genetic mutations for developing disease or research models for any organism can be made and allow the simultaneous editing of any number of target genes just by adding additional guide-strand RNA/donor DNA fusions.

While the above is described using the CRISPR/cpf1 system, as efficient for these purposes, the above approach appears compatiable with a variety of current or future RNA-dependent endonucleases such as cas9 among others.

Figure 6:
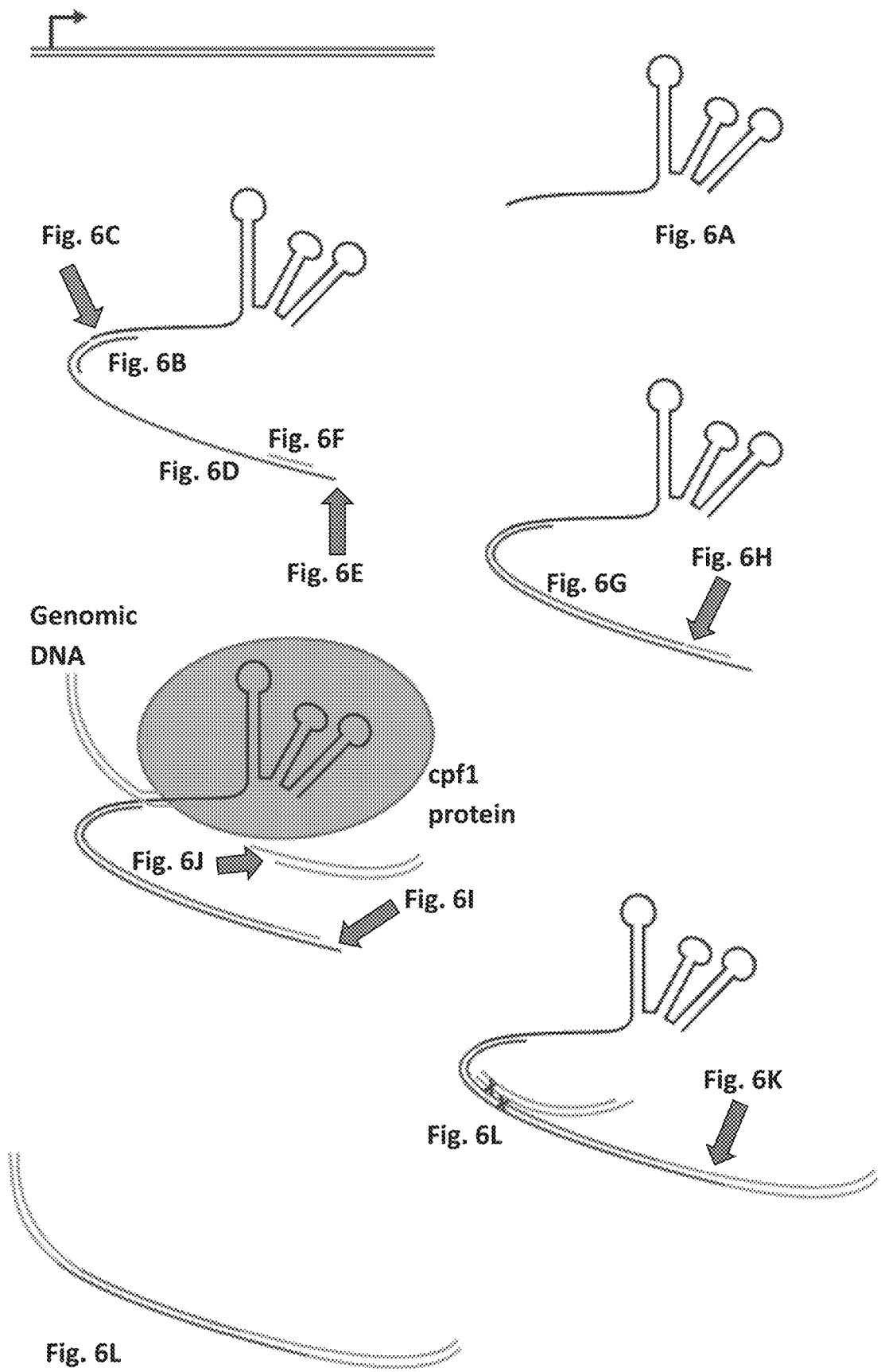
FIG. 6: Parallel multi-locus directed by guide-strand RNA mixture. Begins with T7 RNA synthesis of guide-strand RNA (FIG. 6A), followed by splint (FIG. 6B) mediated ligation (FIG. 6C) of single-stranded donor DNA sequence (FIG. 6D) onto the 5' end of the guide-strand RNA. The 5' nucleotide of the synthesized donor DNA (FIG. 6E) has an exonuclease resistant phosphorothioate bond with its neighboring nucleotide. Thereafter, hybridization of double-stranded DNA terminating oligonucleotide (FIG. 6F) is followed by an isothermal DNA polymerase (Klenow exo-) reaction to fill-in the double strandedness (FIG. 6G) from the splinting primer (step 2) to the terminating oligo (step 3) and T4-DNA ligase reaction (FIG. 611) to complete the donor fragment with the appropriate 5' sticky end (FIG. 6I) for donor DNA sticky end ligation to the sticky end of the genomic DNA (FIG. 6J) digested by cpf1. Complete integration happens upon ligation of the sticky end (FIG. 6K) of the donor DNA and homologous recombination between donor and genomic DNA (FIG. 6L) due to their proximity and sequence homology.

The guide strand/donor fusion is assembled as shown in FIG. 6. More specifically,
1) T7 RNA synthesis of guide-strand RNA (FIG. 6A)
2) Splint (FIG. 6B) mediated ligation (FIG. 6C) of single-stranded donor DNA sequence (FIG. 6D) onto the 5' end of the guide-strand RNA. The 5' nucleotide of the synthesized donor DNA (FIG. 6E) has an exonuclease resistant phosphorothioate bond with its neighboring nucleotide.
3) Hybridization of double-stranded DNA terminating oligonucleotide (FIG. 6F).
4) Isothermal DNA polymerase (Klenow exo-) reaction to fill-in the double strandedness (FIG. 6G) from the splinting primer (step 2) to the terminating oligo (step 3) and T4-DNA ligase reaction (FIG. 6H) to complete the donor fragment with the appropriate 5' sticky end (FIG. 6I) for donor DNA sticky end ligation to the sticky end of the genomic DNA (FIG. 6J) digested by cpf1.
5) Complete integration happens upon ligation of the sticky end (FIG. 6K) of the donor DNA and homologous recombination between donor and genomic DNA (FIG. 6) due to their proximity and sequence homology.
Given the fact that each sgRNA/donor is unique and confers both digestion specificity and the specific donor DNA mutation for the targeted gene, one can combine these hybrid nucleotides with a single protein preparation and get multiple targeted mutations simultaneously.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the compositions for, and methods of, genetic editing, in vivo methods associated with genetic editing, compositions of cells generated by the aforementioned techniques, treatment of diseases and/or conditions that relate to the teachings of the invention, techniques and composition and use of solutions used therein, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventor for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of genomic editing comprising:
contacting a population of cells with a quantity of one or more vectors encoding a fusion protein, said fusion protein comprising a clustered regularly interspaced palindromic repeats (CRISPR)-associated protein (Cas) 9 and a zinc finger domain, wherein the one or more vectors encoding the fusion protein comprises the sequence of SEQ ID NO:1 or encodes the fusion protein of the sequence of SEQ ID NO:2,
contacting the population of cells with one or more single guide RNAs (sgRNAs) or a vector encoding the one or more sgRNAs, and
contacting the population of cells with a donor DNA, said donor DNA comprising a sequence configured for binding the zinc finger domain,
wherein the Cas9 of the fusion protein induces a double stranded break (DSB), which permits homologous recombination (HR) and/or non-homologous end joining (NHEJ) of the DSB, and the donor DNA is brought in proximity to the site of the DSB for integration and thereby editing the genome of the population of cells.

2. The method of claim 1, wherein the donor DNA comprises the sequence of SEQ ID NO:3 and the one or more sgRNAs comprises the sequence of SEQ ID NO:6,
the donor DNA comprises the sequence of SEQ ID NO:4 and the one or more sgRNAs comprises the sequence of SEQ ID NO:7, or
the donor DNA comprises the sequence of SEQ ID NO:5 and the one or more sgRNAs comprises the sequence of SEQ ID NO:8.

3. The method of claim 1, wherein the fusion protein further comprises a nuclear localization signal (NLS) sequence.

4. The method of claim 1, wherein the fusion protein further comprises a fluorescent labeled protein.

5. The method of genomic editing of claim 1, wherein the donor DNA further comprises an expression cassette and two flanking sequences, and wherein the sequence configured for binding the zinc finger domain is not within the expression cassette.

6. The method of claim 5, wherein the sequence configured for binding the zinc finger domain is positioned between the two flanking sequences in the donor DNA.

7. The method of claim 6, wherein the two flanking sequences are each at least 10 base pairs in length, and homologous to sequences in the genome of the population of cells.

8. The method of claim 1, wherein contacting the population of cells comprises performing a technique selected from the group consisting of: transfection, electroporation, and transformation.

9. The method of claim 1, wherein the population of cells comprise stem cells or progenitor cells.

10. The method of claim 7, wherein the two flanking sequences are each at least 80 base pairs in length, wherein a first of the two flanking sequences is positioned 5' and a second of the two flanking sequences is positioned 3' within the donor DNA.

11. The method of claim 1, wherein (i) the donor DNA, (ii) the one or more sgRNAs or the vector encoding the one or more sgRNAs, or (iii) both (i) and (ii), is premixed with the one or more vectors encoding the fusion protein before contacting the population of cells.

* * * * *

SEQUENCE LISTING

```
<160> NUMBER OF SEQ ID NOS: 11

<210> SEQ ID NO 1
<211> LENGTH: 4518
<212> TYPE: DNA
<213> ORGANISM: Artificial Sequence
<220> FEATURE:
<223> OTHER INFORMATION: Cas9

<400> SEQUENCE: 1
atggataaga aatactcaat aggcttagat atcggcacaa atagcgtcgg atgggcggtg      60
atcactgatg aatataaggt tccgtctaaa aagttcaagg ttctgggaaa tacagaccgc     120
```

```
cacagtatca aaaaaaatct tatagggget cttttatttg acagtggaga gacagcggaa    180
gcgactcgtc tcaaacggac agctcgtaga aggtatacac gtcggaagaa tcgtatttgt    240
tatctacagg agattttttc aaatgagatg gcgaaagtag atgatagttt ctttcatcga    300
cttgaagagt cttttttggt ggaagaagac aagaagcatg aacgtcatcc tatttttgga    360
aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca ttttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taagaaaatc ttttttgatc aatcaaaaaa cggatatgca   1080
ggttatattg atgggggagc tagccaagaa gaattttata aatttatcaa accaattttta   1140 gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagcaagaa agacttttat ccatttttaa aagacaatcg tgagaagatt   1320
gaaaaaatct tgactttcg aattccttat tatgttggtc cattggcgcg tggcaatagt   1380
cgttttgcat ggatgactcg gaagtctgaa gaaacaatta ccccatgaa ttttgaagaa   1440 gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaagaaga ttatttcaaa aaaatagaat gttttgatag tgttgaaatt   1740
tcaggagttg aagatagatt taatgcttca ttaggtacct accatgattt gctaaaaatt   1800
attaaagata aagattttt ggataatgaa gaaaatgaag atatcttaga ggatattgtt   1860
ttaacattga cctatttga agataggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040 gatttttga aatcagatgg ttttgccaat cgcaattta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
```

```
gacatgtatg tggaccaaga attagatatt aatcgtttaa gtgattatga tgtcgatcac    2520
attgttccac aaagtttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtga gattaacaat     2940 taccatcatg cccatgatgc gtatctaaat gccgtcgttg aactgctttt gattaagaaa    3000
tatccaaaac ttgaatcgga gtttgtctat ggtgattata agtttatga tgttcgtaaa     3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taggaagtt aaaaaagact taatcattaa actacctaaa    3600 tatagtctt ttgagttaga aaacggtcgt aaacggatgc tggctagtgc cggagaatta    3660 caaaaggaa atgagctggc tctgccaagc aaatatgtga ttttttata tttagctagt    3720 cattatgaaa agttgaaggg tagtccagaa gataacgaac aaaaacaatt gtttgtggag    3780
cagcataagc attatttaga tgagattatt gagcaaatca gtgaattttc taagcgtgtt    3840
attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac gtctacaaaa    4020 gaagttttag atgccactct tatccatcaa tccatcactg gtctttatga aacacgcatt    4080
gatttgagtc agctaggagg tgactctagc gctggagcgg gtgcagggc tcccgggttc     4140 cagtgccgga tctgcatgcg gaacttcagc gaccggtcca acctgagcag gcacatcaga    4200
acccacaccg gagaaaagcc cttcgcctgc gacatttgcg gccggaagtt cgccatcagc    4260
agcaacctga cagccacac caagatccac actggcagcc agaaaccttt ccagtgcaga    4320
atttgtatga gaaactttag cagaagcgac aacctggcca gacacatccg gacacatact    4380
ggtgaaaaac cttttgcctg tgatatctgt ggcagaaagt ttgccacctc cggcaatctg    4440
acccggcaca caaagattca cctgcggggc agccagctgt ggcgcctacc caagaagaag    4500
aggaaagtct ctagatag                                                  4518
```

<210> SEQ ID NO 2
<211> LENGTH: 1505
<212> TYPE: PRT
<213> ORGANISM: Artificial Sequence
<220> FEATURE:
<223> OTHER INFORMATION: Cas9

<400> SEQUENCE: 2

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415
```

-continued

Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
            610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
            770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys

-continued

```
             835                 840                 845
Asp Asp Ser Ile Asp Asn Lys Val Leu Thr Arg Ser Asp Lys Asn Arg
         850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                 885                 890                 895
Phe Asp Asn Leu Thr Lys Ala Glu Arg Gly Gly Leu Ser Glu Leu Asp
             900                 905                 910
Lys Ala Gly Phe Ile Lys Arg Gln Leu Val Glu Thr Arg Gln Ile Thr
             915                 920                 925
Lys His Val Ala Gln Ile Leu Asp Ser Arg Met Asn Thr Lys Tyr Asp
         930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
             965                 970                 975
Glu Ile Asn Asn Tyr His His Ala His Asp Ala Tyr Leu Asn Ala Val
             980                 985                 990
Val Gly Thr Ala Leu Ile Lys Lys  Tyr Pro Lys Leu Glu  Ser Glu Phe
             995                 1000                1005
Val Tyr Gly Asp Tyr Lys Val  Tyr Asp Val Arg Lys  Met Ile Ala
    1010                1015                1020
Lys Ser  Glu Gln Glu Ile Gly  Lys Ala Thr Ala Lys  Tyr Phe Phe
    1025                1030                1035
Tyr Ser  Asn Ile Met Asn Phe  Phe Lys Thr Glu Ile  Thr Leu Ala
    1040                1045                1050
Asn Gly  Glu Ile Arg Lys Arg  Pro Leu Ile Glu Thr  Asn Gly Glu
    1055                1060                1065
Thr Gly  Glu Ile Val Trp Asp  Lys Gly Arg Asp Phe  Ala Thr Val
    1070                1075                1080
Arg Lys  Val Leu Ser Met Pro  Gln Val Asn Ile Val  Lys Lys Thr
    1085                1090                1095
Glu Val  Gln Thr Gly Gly Phe  Ser Lys Glu Ser Ile  Leu Pro Lys
    1100                1105                1110
Arg Asn  Ser Asp Lys Leu Ile  Ala Arg Lys Lys Asp  Trp Asp Pro
    1115                1120                1125
Lys Lys  Tyr Gly Gly Phe Asp  Ser Pro Thr Val Ala  Tyr Ser Val
    1130                1135                1140
Leu Val  Val Ala Lys Val Glu  Lys Gly Lys Ser Lys  Lys Leu Lys
    1145                1150                1155
Ser Val  Lys Glu Leu Leu Gly  Ile Thr Ile Met Glu  Arg Ser Ser
    1160                1165                1170
Phe Glu  Lys Asn Pro Ile Asp  Phe Leu Glu Ala Lys  Gly Tyr Lys
    1175                1180                1185
Glu Val  Lys Lys Asp Leu Ile  Ile Lys Leu Pro Lys  Tyr Ser Leu
    1190                1195                1200
Phe Glu  Leu Glu Asn Gly Arg  Lys Arg Met Leu Ala  Ser Ala Gly
    1205                1210                1215
Glu Leu  Gln Lys Gly Asn Glu  Leu Ala Leu Pro Ser  Lys Tyr Val
    1220                1225                1230
Asn Phe  Leu Tyr Leu Ala Ser  His Tyr Glu Lys Leu  Lys Gly Ser
    1235                1240                1245
```

```
Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Ser Ala Gly Ala Gly Ala Gly Ala Pro Gly Phe Gln Cys Arg
    1370                1375                1380

Ile Cys Met Arg Asn Phe Ser Asp Arg Ser Asn Leu Ser Arg His
    1385                1390                1395

Ile Arg Thr His Thr Gly Glu Lys Pro Phe Ala Cys Asp Ile Cys
    1400                1405                1410

Gly Arg Lys Phe Ala Ile Ser Ser Asn Leu Asn Ser His Thr Lys
    1415                1420                1425

Ile His Thr Gly Ser Gln Lys Pro Phe Gln Cys Arg Ile Cys Met
    1430                1435                1440

Arg Asn Phe Ser Arg Ser Asp Asn Leu Ala Arg His Ile Arg Thr
    1445                1450                1455

His Thr Gly Glu Lys Pro Phe Ala Cys Asp Ile Cys Gly Arg Lys
    1460                1465                1470

Phe Ala Thr Ser Gly Asn Leu Thr Arg His Thr Lys Ile His Leu
    1475                1480                1485

Arg Gly Ser Gln Leu Trp Arg Leu Pro Lys Lys Lys Arg Lys Val
    1490                1495                1500

Ser Arg
    1505

<210> SEQ ID NO 3
<211> LENGTH: 883
<212> TYPE: DNA
<213> ORGANISM: Artificial Sequence
<220> FEATURE:
<223> OTHER INFORMATION: Super Folder GFP

<400> SEQUENCE: 3
ctaaggactc ggcgcgccgg aagtggccag ggcgggggcg acctcggctc acagcgcgcc      60
cggctattct cgcagctcag gtcatcctca tcatgagtaa aggcgaagag ctgttcactg     120
gtgtcgtccc tattctggtg gaactggatg gtgatgtcaa cggtcataag ttttccgtgc     180
gtggcgaggg tgaaggtgac gcaactaatg gaaactgac gctgaagttc atctgtacta     240
ctgggaaact gccggtgcct tggccgactt tagtaacgac gctgactat ggtgttcagt     300 gctttgctcg ttatccggac catatgaagc agcatgactt cttcaagtcc gccatgccgg     360
aaggctatgt gcaggaacgc acgatttcct tcaaagatga cggcacgtac aaaacgcgtg     420
```

```
cggaagtgaa atttgaaggc gatactttag taaaccgcat tgagttgaaa ggcattgact    480
ttaaagaaga cggcaatatc ctgggccata agctggaata caattttaac agccacaatg    540
tttacatcac cgccgataaa caaaaaaatg gcattaaagc gaattttaaa attcgccaca    600
acgtggagga tggcagcgtg cagctggctg atcactacca gcaaaacact ccaatcggtg    660
atggtcctgt tctgctgccg gacaatcact atctgagcac gcaaagcgtt ttgtctaagg    720
acccgaacga gaaacgcgat catatggttc tgctggagtt cgtaaccgca gcgggcatca    780
cgcatggaat ggatgaatta tatgggtcca aaaccatgga tgatgatatc gccgcgctcg    840
tcgtcgacaa cggctccggc atgtgcaagg ccggcttcgc ggg                      883
```

```
<210> SEQ ID NO 4
<211> LENGTH: 1251
<212> TYPE: DNA
<213> ORGANISM: Artificial Sequence
<220> FEATURE:
<223> OTHER INFORMATION: Sox-2-mOrange

<400> SEQUENCE: 4
ccggggcgga ggtgcaggac cagagcgcgc agagcagact gcacatgtcc caacattacc    60
agagcgcacc tgtgcccggt accatcaatg gtaccatccc gctgagccac atgggtggag   120
gttctggtgg aggatccgga ggtggatcag gaggaggttc ggtgagcaag ggcgaggaga   180
ataatatggc catcattaag gagttcatgc gcttcaaggt gcacatggag ggcactgtga   240
acggccacga gttcgagatc gagggcgagg gcgagggcca ccctacgag ggctttcaga    300
ccgctaagct gaaggtgacc aagggcggcc ccctgccctt cgcctgggac atcctgtccc   360
ctctcatcac ctacggctcc aaggcctacg tgaagcaccc cgccgacatc cccgactact   420
tcaagctgtc cttccccgag ggcttcaagt gggagcgcgt gatgaactac gaggacggcg   480
gcgtggtgac cgtgacccag gactcctctc tgcaggacgg cgagttcatc tacaaggtga   540
agatgcgcgg caccaacttc ccctccgacg gccccgtgat gcagaagaag accatgggct   600
gggaggcctc ctccgagcgg atgtaccccg aggacggcgc cctgaagggc gagatcagga   660
tgaggctgaa gctgaaggat ggcggccact acacctccga ggtcaagact acctacaagg   720
ccaagaagtc cgtgctgctg cccggcgcct acatcgtcgg catcaagctg gacatcacct   780
cccacaacga ggactacacc atcgtggaac agtacgaacg ctccgaggcc cgccactcca   840
ccggcggcat ggacgagctg tacaagtaaa gcggccgcga ctctagatca taatcagcca   900
taccacattt gtagaggttt tacttgcttt aaaaaacctc ccacacctcc ccctgaacct   960
gaaacataaa atgaatgcaa ttggtcatcc tcatcgcccg gatagctcag tcggtagagc   1020
agcggccgga tgtaactgaa tgaaatggtg aaggacgggt ccagtaggct gcttcggcag   1080
cctacttgtt gagtagagtg tgagctccgt aactagttac atccggccgc gggtccaggg   1140
ttcaagtccc tgttcgggcg ccagaattct aaaatgaact cttttttacta cactgctgga  1200
ctatttttgt acagaacact tcttttgggg agggaaaaag ttgtatagag c            1251
```

```
<210> SEQ ID NO 5
<211> LENGTH: 931
<212> TYPE: DNA
<213> ORGANISM: Artificial Sequence
<220> FEATURE:
<223> OTHER INFORMATION: Oct-4-GFP

<400> SEQUENCE: 5
ccacactcta ctcagtccct tttcctgagg gcgaggcctt tccctctgtt cccgtcactg    60
```

```
ctctgggctc tcccatgcat tcaaactcta gcgctggagc gggtgcaggg gctaaaggcg    120
aagagctgtt cactggtgtc gtccctattc tggtggaact ggatggtgat gtcaacggtc    180
ataagttttc cgtgcgtggc gagggtgaag gtgacgcaac taatgggaaa ctgacgctga    240
agttcatctg tactactggg aaactgccgg tgccttggcc gactttagta acgacgctga    300
cttatggtgt tcagtgcttt gctcgttatc cggaccatat gaagcagcat gacttcttca    360
agtccgccat gccggaaggc tatgtgcagg aacgcacgat ttccttcaaa gatgacggca    420
cgtacaaaac gcgtgcggaa gtgaaatttg aaggcgatac tttagtaaac cgcattgagt    480
tgaaaggcat tgactttaaa gaagacggca atatcctggg ccataagctg aatacaatt    540 ttaacagcca caatgtttac atcaccgccg ataaacaaaa aaatggcatt aaagcgaatt    600
ttaaaattcg ccacaacgtg gaggatggca gcgtgcagct ggctgatcac taccagcaaa    660
acactccaat cggtgatggt cctgttctgc tgccggacaa tcactatctg agcacgcaaa    720
gcgttttgtc taaggacccg aacgagaaac gcgatcatat ggttctgctg gagttcgtaa    780
ccgcagcggg catcacgcat ggaatggatg aattatataa ataagtcatc ctcatcctga    840
ggcaccagcc ctccctgggg atgctgtgag ccaaggcaag ggaggtagac aagagaacct    900
ggagctttgg ggttaaattc tttactgag g    931

<210> SEQ ID NO 6
<211> LENGTH: 100
<212> TYPE: RNA
<213> ORGANISM: Homo sapiens

<400> SEQUENCE: 6
gcuauucucg cagcucacca guuuuagagc uagaaauagc aaguuaaaau aaggcuaguc    60
cguuaucaac uugaaaaagu ggcaccgagu cggugcuuuu    100

<210> SEQ ID NO 7
<211> LENGTH: 100
<212> TYPE: RNA
<213> ORGANISM: D. rerio

<400> SEQUENCE: 7
gugcccggua cgacgauuaa guuuuagagc uagaaauagc aaguuaaaau aaggcuaguc    60
cguuaucaac uugaaaaagu ggcaccgagu cggugcuuuu    100

<210> SEQ ID NO 8
<211> LENGTH: 100
<212> TYPE: RNA
<213> ORGANISM: Mus musculus

<400> SEQUENCE: 8
ccuuggcuca cagcaucccc guuuuagagc uagaaauagc aaguuaaaau aaggcuaguc    60
cguuaucaac uugaaaaagu ggcaccgagu cggugcuuuu    100

<210> SEQ ID NO 9
<211> LENGTH: 9
<212> TYPE: PRT
<213> ORGANISM: Artificial Sequence
<220> FEATURE:
<223> OTHER INFORMATION: synthesized

<400> SEQUENCE: 9

Ser Ser Ala Gly Ala Gly Ala Gly Ala
1               5
```

```
<210> SEQ ID NO 10
<211> LENGTH: 4
<212> TYPE: PRT
<213> ORGANISM: Artificial Sequence
<220> FEATURE:
<223> OTHER INFORMATION: synthesized

<400> SEQUENCE: 10

Trp Arg Leu Pro
1

<210> SEQ ID NO 11
<211> LENGTH: 4
<212> TYPE: PRT
<213> ORGANISM: Artificial Sequence
<220> FEATURE:
<223> OTHER INFORMATION: synthesized

<400> SEQUENCE: 11

Thr Thr Thr Asn
1
```